(12) United States Patent
Ho et al.

(10) Patent No.: US 8,030,029 B2
(45) Date of Patent: Oct. 4, 2011

(54) FLU VACCINES AND METHODS OF USE THEREOF

(75) Inventors: David D. Ho, Chappaqua, NY (US); Yaoxing Huang, Brooklyn, NY (US); Ming Wei Chen, Taipei (TW); Rachel TJ Cheng, Taipei (TW); Chi-Huey Wong, La Jolla, CA (US); Alice Yu, La Jolla, CA (US)

(73) Assignees: Academia Sinica, Taipei (TW); The Rockefeller University, New York, NY (US)

( * ) Notice: Subject to any disclaimer, the term of this patent is extended or adjusted under 35 U.S.C. 154(b) by 0 days.

(21) Appl. No.: 12/011,032

(22) Filed: Jan. 23, 2008

(65) Prior Publication Data

US 2009/0060949 A1 Mar. 5, 2009

Related U.S. Application Data

(60) Provisional application No. 60/897,062, filed on Jan. 24, 2007.

(51) Int. Cl.
*C12N 15/44* (2006.01)
*A61K 48/00* (2006.01)

(52) U.S. Cl. .................. 435/69.3; 514/44 R; 424/210.1; 536/23.72

(58) Field of Classification Search ........................ None
See application file for complete search history.

(56) References Cited

U.S. PATENT DOCUMENTS

2007/0286873 A1* 12/2007 Williams et al. ........... 424/210.1
2009/0208531 A1* 8/2009 Nabel et al. ................ 424/209.1

FOREIGN PATENT DOCUMENTS

WO  WO 2006/119516  * 11/2006
WO  WO 2007/100584  * 9/2007

OTHER PUBLICATIONS

Boltz et al. H5N1 Influenza Viruses in Lao People's Democratic Republic. Emerging Infectious Diseases. Oct. 2006. vol. 12, No. 10, p. 1593-1595.
NCBI locus ABG67978, Hemagglutinin [Influenza A Virus (A/duck/laos/3295/2006(H5N1))]. Oct. 8, 2006.
International Search Report; PCT/US08/00919; Jul. 1, 2008.

* cited by examiner

*Primary Examiner* — Mary E Mosher
(74) *Attorney, Agent, or Firm* — Shantanu Basu; Eckman Basu LLP

(57) ABSTRACT

This disclosure is directed, inter alia, to polynucleotides, polypeptides, vectors, cells and compositions comprising the same, and their use in affecting viral pathogenesis, in particular for influenza viral infection.

5 Claims, 29 Drawing Sheets

FIGURE 1: Phylogenetic Analysis Of The H5N1 Hemagglutinin Protein

- 001 VN/1203/2004
- 004 cat/Thailand/KU-02/04
- 002 VN/1194/2004 (NIBRG-14)
- 005 dog/Thailand-Suphanburi/KU Clade 1

- Consensus (HAc)
- 003 HK/213/03 (HK)
- 021 ck/HK/220/97
- 022 human/HK/156/97
- 009 ck/Indonesia/5/2004 (ID)
- 006 Indonesia/6/2005
- 007 Indonesia/7/2005
- 008 Indonesia/5/2005 (NIBRG-2) (IDS)

Clade 2 Subclade 1

- 013 bhg/Qinghai/62/2005 (QH)
- 010 turkey/Turkey/1/2005 (NIBRG-23)
- 011 ws/Mongolia/244/2005
- 012 bhg/Qinghai/1A/2005

Clade 2 Subclade 2

- 018 dk/China/E319-2/03 (Tamsui strain)
- 019 gh/HK/728/2004
- 020 ck/Guangdong/178/04
- 017 dk/Fujian/9713/2005
- 016 gr/Taichung/Q156/05
- 014 Anhui/1/2005 (Anhui)
- 015 dk/Fujian/1734/05 (FJ-like)

Clade 2 Subclade 3

0.01

FIGURE 2: Optimized Consensus HA Amino Acid Sequence

```
M E K I V L L F A I V S L V K S
D Q I C I G Y H A N N S T E Q V
D T I M E K N V T V T H A Q D I
L E K T H N G K L C D L D G V K
P L I L R D C S V A G W L L G N
P M C D E F I N V P E W S Y I V
E K A N P A N D L C Y P G D F N
D Y E E L K H L L S R I N H F E
K I Q I I P K S S W S S H E A S
S G V S S A C P Y Q G K S S F F
R N V V W L I K K N S T Y P T I
K R S Y N N T N Q E D L L V L W
G I H H P N D A A E Q T K L Y Q
N P T T Y I S V G T S T L N Q R
L V P K I A T R S K V N G Q S G
R M E F F W T I L K P N D A I N
F E S N G N F I A P E Y A Y K I
V K K G D S T I M K S E L E Y G
N C N T K C Q T P M G A I N S S
M P F H N I H P L T I G E C P K
Y V K S N R L V L A T G L R N S
P Q R E R R R K K R G L F G A I
A G F I E G G W Q G M V D G W Y
G Y H H S N E Q G S G Y A A D K
E S T Q K A I D G V T N K V N S
I I D K M N T Q F E A V G R E F
N N L E R R I E N L N K K M E D
G F L D V W T Y N A E L L V L M
E N E R T L D F H D S N V K N L
Y D K V R L Q L R D N A K E L G
N G C F E F Y H K C D N E C M E
S V R N G T Y D Y P Q Y S E E A
R L K R E E I S G V K L E S I G
I Y Q I L S I Y S T V A S S L A
L A I M V A G L S L W M C S N G
S L Q C R I C I
```

FIGURE 3: Optimized HAc Nucleic Acid Sequence

```
ATG GAG AAG ATC GTG CTG CTG TTC GCC ATC GTG AGC CTG GTG AAG AGC
GAC CAG ATC TGC ATC GGA TCC CAC GCC AAC AAC AGC ACC GAG CAG GTG
GAC ACC ATC ATG GAG AAG AAC GTG ACC GTG ACC CAC GCC CAG GAC ATC
CTG GAG AAG ACC CAC AAC GGC AAG CTG TGC GAC CTG GAC GGC GTG AAG
CCT CTG ATC CTG AGA GAC TGC AGC GTG GCC GGC TGG CTG CTG GGC AAC
CCT ATG TGC GAC GAG TTC ATC AAC GTG CCT GAG TGG AGC TAC ATC GTG
GAG AAG GCC AAC CCT GCC AAC GAC CTG TGC TAC CCT GGC GAC TTC AAC
GAC TAC GAG GAG CTG AAG CAC CTG CTG AGC AGA ATC AAC CAC TTC GAG
AAG ATC CAG ATC ATC CCT AAG AGC AGC TGG AGC AGC CAC GAG GCC AGC
AGC GGC GTG AGC AGC GCC TGC CCT TAC CAG GGC AAG AGC AGC TTC TTC
AGA AAC GTG GTG TGG CTG ATC AAG AAG AAC AGC ACC TAC CCT ACC ATC
AAG AGA AGC TAC AAC AAC ACC AAC CAG GAG GAC CTG CTG GTG CTG TGG
GGC ATC CAC CAC CCT AAC GAC GCC GCC GAG CAG ACC AAG CTG TAC CAG
AAC CCT ACC ACC TAC ATC AGC GTG GGC ACC AGC ACC CTG AAC CAG AGA
CTG GTG CCT AAG ATC GCC ACC AGA AGC AAG GTG AAC GGC CAG AGC GGC
AGA ATG GAG TTC TTC TGG ACC ATC CTG AAG CCT AAC GAC GCC ATC AAC
TTC GAG AGC AAC GGC AAC TTC ATC GCC CCT GAG TAC GCC TAC AAG ATC
GTG AAG AAG GGC GAC AGC ACC ATC ATG AAG AGC GAG CTG GAG TAC GGC
AAC TGC AAC ACC AAG TGC CAG ACC CCT ATG GGC GCC ATC AAC AGC AGC
ATG CCT TTC CAC AAC ATC CAC CCT CTG ACC ATC GGC GAG TGC CCT AAG
TAC GTG AAG AGC AAC AGA CTG GTG CTG GCC ACC GGC CTG AGA AAC AGC
CCT CAG AGA GAG AGA AGA AGA AAG AAG AGA GGC CTG TTC GGC GCC ATC
GCC GGC TTC ATC GAG GGC GGC TGG CAG GGC ATG GTG GAC GGC TGG TAC
GGC TAC CAC CAC AGC AAC GAG CAG GGC AGC GGC TAC GCC GCC GAC AAG
GAG AGC ACC CAG AAG GCC ATC GAC GGC GTG ACC AAC AAG GTG AAC AGC
ATC ATC GAC AAG ATG AAC ACC CAG TTC GAG GCC GTG GGC AGA GAG TTC
AAC AAC CTG GAG AGA AGA ATC GAG AAC CTG AAC AAG AAG ATG GAG GAC
GGC TTC CTG GAC GTG TGG ACC TAC AAC GCC GAG CTG CTG GTG CTG ATG
GAG AAC GAG AGA ACC CTG GAC TTC CAC GAC AGC AAC GTG AAG AAC CTG
TAC GAC AAG GTG AGA CTG CAG CTG AGA GAC AAC GCC AAG GAG CTG GGC
AAC GGC TGC TTC GAG TTC TAC CAC AAG TGC GAC AAC GAG TGC ATG GAG
AGC GTG AGA AAC GGC ACC TAC GAC TAC CCT CAG TAC AGC GAG GAG GCC
AGA CTG AAG AGA GAG GAG ATC AGC GGC GTG AAG CTG GAG AGC ATC GGC
ATC TAC CAG ATC CTG AGC ATC TAC AGC ACC GTG GCC AGC AGC CTG GCC
CTG GCC ATC ATG GTG GCC GGC CTG AGC CTG TGG ATG TGC AGC AAC GGC
AGC CTG CAG TGC AGA ATC TGC ATC
```

FIGURE 4: Optimized HA5 of RG2 (Indonesia/5/2005) Amino Acid Sequence

```
M E K I V L L A I V S L V K S
D Q I C I G Y H A N N S T E Q V
D T I M E K N V T V T H A Q D I
L E K T H N G K L C D L D G V K
P L I L R D C S V A G W L L G N
P M C D E F I N V P E W S Y I V
E K A N P T N D L C Y P G S F N
D Y E E L K H L L S R I N H F E
K I Q I I P K S S W S D H E A S
S G V S S A C P Y L G S P S F F
R N V V W L I K K N N T Y P T I
K K S Y N N T N Q E D L L V L W
G I H H P N D A A E Q T R L Y Q
N P T T Y I S I G T S T L N Q R
L V P K I A T R S K V N G Q S G
R M E F F W T I L K P N D A I N
F E S N G N F I A P E Y A Y K I
V K K G D S A I M K S E L E Y G
N C N T K C Q T P M G A I N S S
M P F H N I H P L T I G E C P K
Y V K S N Q L V L A T G L R N S
P Q R E S R R K K R G L F G A I
A G F I E G G W Q G M V D G W Y
G Y H H S N E Q G S G Y A A D K
E S T Q K A I D G V T N K V N S
I I D K M N T Q F E A V G R E F
N N L E R R I E N L N K K M E D
G F L D V W T Y N A E L L V L M
E N E R T L D F H D S N V K N L
Y D K V R L Q L R D N A K E L G
N G C F E F Y H K C D N E C M E
S I R N G T Y N Y P Q Y S E E A
R L K R E E I S G V K L E S I G
T Y Q I L S I Y S T V A S S L A
L A I M M A G L S L W M C S N G
S L Q C R I C I
```

FIGURE 5: Optimized HA5 of RG2 (Indonesia/5/2005) Nucleic Acid Sequence (ID5)

ATG GAG AAG ATC GTG CTG CTC GCC ATC GTG AGC CTG GTG AAG AGC
GAC CAG ATC TGC ATC GGA TCC CAC GCC AAC AAC AGC ACC GAG CAG GTG
GAC ACC ATC ATG GAG AAG AAC GTG ACC GTG ACC CAC GCC CAG GAC ATC
CTG GAG AAG ACC CAC AAC GGC AAG CTG TGC GAC CTG GAC GGC GTG AAG
CCT CTG ATC CTG AGA GAC TGC AGC GTG GCC GGC TGG CTG CTG GGC AAC
CCT ATG TGC GAC GAG TTC ATC AAC GTG CCT GAG TGG AGC TAC ATC GTG
GAG AAG GCC AAC CCT ACC AAC GAC CTG TGC TAC CCT GGC TCC TTC AAC
GAC TAC GAG GAG CTG AAG CAC CTG CTG AGC AGA ATC AAC CAC TTC GAG
AAG ATC CAG ATC ATC CCT AAG AGC AGC TGG AGC GAC CAC GAG GCC AGC
AGC GGC GTG AGC AGC GCC TGC CCT TAC CTG GGC TCG CCC AGC TTC TTC
AGA AAC GTG GTG TGG CTG ATC AAG AAG AAC AGC ACC TAC CCT ACC ATC
AAG AAA AGC TAC AAC AAC ACC AAC CAG GAG GAC CTG CTG GTG CTG TGG
GGC ATC CAC CAC CTC AAC GAC GCC GCC GAG CAG ACC AAG CTG TAC CAG
AAC CCT ACC ACC TAC ATC AGC ATC GGC ACC AGC ACC CTG AAC CAG AGA
CTG GTG CCT AAG ATC GCC ACC AGA AGC AAG GTG AAC GGC CAG AGC GGC
AGA ATG GAC TTC TTC TGG ACC ATC CTG AAG CCT AAC GAC GCC ATC AAC
TTC GAG AGC AAC GGC AAC TTC ATC GCC CCT GAG TAC GCC TAC AAG ATC
GTG AAG AAA GGC GAC AGC GCC ATC ATG AAG AGC GAG CTG GAG TAC GGC
AAC TGC AAC ACC AAG TGC CAG ACC CCT ATC GGC GCC ATC AAC AGC AGC
ATG CCT TTC CAC AAC ATC CAC CCT CTG ACC ATC GGC GAG TGC CCT AAG
TAC GTG AAG AGC AAC AGA CTG GTG CTG GCC ACC GGC CTG AGA AAC AGC
CCT CAG AGA GAG TCA AGA AGA AAG AGA GGC CTG TTC GGC GCC ATC
GCC GGC TTC ATC GAG GGC GGC TGG CAG GGC ATG GTG GAC GGC TGG TAC
GGC TAC CAC CAC AGC AAC GAG CAG GGC AGC GGC TAC GCC GCC GAC AAG
GAG AGC ACC CAG AAG GCC ATC GAC GGC GTG ACC AAC AAG GTG AAC AGC
ATC ATC GAC AAG ATG AAC ACC CAG TTC GAG GCC GTG GGC AGA GAG TTC
AAC AAC CTG GAG AGA AGA ATC GAG AAC CTG AAC AAG AAG ATG GAG GAC
GGC TTC CTG GAC GTG TGG ACC TAC AAC GCC GAG CTG CTG GTG CTG ATG
GAG AAC GAG AGA ACC CTG GAC TTC CAC GAC AGC AAC GTG AAG AAC CTG
TAC GAC AAG GTG AGA CTG CAG CTG AGA GAC AAC GCC AAG GAG CTG GGC
AAC GGC TGC TTC GAG TTC TAC CAC AAG TGC GAC AAC GAG TGC ATG GAG
AGC ATC AGA AAC GGC ACC TAC AAC TAC CCT CAG TAC AGC GAG GAG GCC
AGA CTG AAG AGA GAG GAG ATC AGC GGC GTG AAG CTG GAG AGC ATC GGC
ACC TAC CAG ATC CTG AGC ATC TAC AGC ACC GTG GCC AGC AGC CTG GCC
CTG GCC ATC ATG ATG GCC GGC CTG AGC CTG TGG ATG TGC AGC AAC GGC
AGC CTG CAG TGC AGA ATC TGC ATC

FIGURE 6: Optimized H5 of RG5 (Anhui/05/2005 9H5N1)/PR8-IBCDC-RG5 Amino Acid Sequence

```
M E K I V L L L A I V S L V K S
D Q I C I G Y H A N N S T E Q V
D T I M E K N V T V T H A Q D I
L E K T H N G K L C D L D G V K
P L I R D C S V A G W L L G N
P M C D E F I N V P E W S Y I V
E K A N P A N D L C Y P G N F N
D Y E E L K H L L S R I N H F E
K I Q I I P K S S W S D H E A S
S G V S S A C P Y Q G T P S F F
R N V V W L I K K N N T Y P T I
K R S Y N N T N Q E D L L I L W
G I H H S N D A A E Q T K L Y Q
N P T T Y I S V G T S T L N Q R
L V P K I A T R S K V N G Q S G
R M D F F W T I L K P N D A I N
F E S N G N F I A P E Y A Y K I
V K K G D S A I M K S E V E Y G
N C N T M C Q T P I G A I N S S
M P F H N I H P L T I G E C P K
Y V K S N K L V L A T G L R N S
P L R E R R R K K R G L F G A I
A G F I E G G W Q G M V D G W Y
G Y H H S N E Q G S G Y A A D K
E S T Q K A I D G V T N K V N S
I I D K M N T Q F E A V G R E F
N N L E R R I E N L N K K M E D
G F L D V W T Y N A E L L V L M
E N E R T L D F H D S N V K N L
Y D K V R L Q L R D N A K E L G
N G C F E F Y H K C D N E C M E
S V R N G T Y D Y P Q Y S E E A
R L K R E E I S G V K L E S I G
T Y Q I L S I Y S T V A S S L A
L A I M V A G L S L W M C S N G
S L Q C R I C I
```

FIGURE 7: Optimized H5 of RG5 (Anhui/05/2005 9H5N1)/PR8-IBCDC-RG5 Nucleic Acid Sequence (_Anhui)

```
ATG GAG AAG ATC GTG CTG CTC GCC ATC GTG AGC CTG GTG AAG AGC
GAC CAG ATC TGC ATC GGA TCC CAC GCC AAC AAC AGC ACC GAG CAG GTG
GAC ACC ATC ATG GAG AAG AAC GTG ACC GTG ACC CAC GCC CAG GAC ATC
CTG GAG AAG ACC CAC AAC GGC AAG CTG TGC GAC CTG GAC GGC GTG AAG
CCT CTG ATC CTG AGA GAC TGC AGC GTG GCC GGC TGG CTG CTG GGC AAC
CCT ATG TGC GAC GAG TTC ATC AAC GTG CCT GAG TGG AGC TAC ATC GTG
GAG AAG GCC AAC CCT GCC AAC GAC CTG TGC TAC CCT GGC AAC TTC AAC
GAC TAC GAG GAG CTG AAG CAC CTG CTG AGC AGA ATC AAC CAC TTC GAG
AAG ATC CAG ATC ATC CCT AAG AGC AGC TGG AGC GAC CAC GAG GCC AGC
AGC GGC GTG AGC AGC GCC TGC CCT TAC CAG GGC ACG CCC AGC TTC TTC
AGA AAC GTG GTG TGG CTG ATC AAG AAG AAC AAC ACC TAC CCT ACC ATC
AAG AGA AGC TAC AAC AAC ACC AAC CAG GAG GAC CTG CTG ATC CTG TGG
GGC ATC CAC CAC TCT AAC GAC GCC GCC GAG CAG ACC AAG CTG TAC CAG
AAC CCT ACC ACC TAC ATC AGC GTG GGC ACC AGC ACC CTG AAC CAG AGA
CTG GTG CCT AAG ATC GCC ACC AGA AGC AAG GTG AAC GGC CAG AGC GGC
AGA ATG GAC TTC TTC TGG ACC ATC CTG AAG CCT AAC GAC GCC ATC AAC
TTC GAG AGC AAC GGC AAC TTC ATC GCC CCT GAG TAC GCC TAC AAG ATC
GTG AAG AAA GGC GAC AGC GCC ATC ATG AAG AGC GAG GTG GAG TAC GGC
AAC TGC AAC ACC ATG TGC CAG ACC CCT ATC GGC GCC ATC AAC AGC AGC
ATG CCT TTC CAC AAC ATC CAC CCT CTG ACC ATC GGC GAG TGC CCT AAG
TAC GTG AAG AGC AAC AAA CTG GTG CTG GCC ACC GGC CTG AGA AAC AGC
CCT CTG AGA GAG AGA AGA AGA AAG AGA GGC CTG TTC GGC GCC ATC
GCC GGC TTC ATC GAG GGC GGC TGG CAG GGC ATG GTG GAC GGC TGG TAC
GGC TAC CAC CAC AGC AAC GAG CAG GGC AGC GGC TAC GCC GCC GAC AAG
GAG AGC ACC CAG AAG GCC ATC GAC GGC GTG ACC AAC AAG GTG AAC AGC
ATC ATC GAC AAG ATG AAC ACC CAG TTC GAG GCC GTG GGC AGA GAG TTC
AAC AAC CTG GAG AGA AGA ATC GAG AAC CTG AAC AAG AAG ATG GAG GAC
GGC TTC CTG GAC GTG TGG ACC TAC AAC GCC GAG CTG CTG GTG CTG ATG
GAG AAC GAG AGA ACC CTG GAC TTC CAC GAC AGC AAC GTG AAG AAC CTG
TAC GAC AAG GTG AGA CTG CAG CTG AGA GAC AAC GCC AAG GAG CTG GGC
AAC GGC TGC TTC GAG TTC TAC CAC AAG TGC GAC AAC GAG TGC ATG GAG
AGC GTG AGA AAC GGC ACC TAC GAC TAC CCT CAG TAC AGC GAG GAG GCC
AGA CTG AAG AGA GAG GAG ATC AGC GGC GTG AAG CTG GAG AGC ATC GGC
ACC TAC CAG ATC CTG AGC ATC TAC AGC ACC GTG GCC AGC AGC CTG GCC
CTG GCC ATC ATG GTG GCC GGC CTG AGC CTG TGG ATG TGC AGC AAC GGC
AGC CTG CAG TGC AGA ATC TGC ATC
```

FIGURE 8 Characterization Of The DNA HAc Vaccine

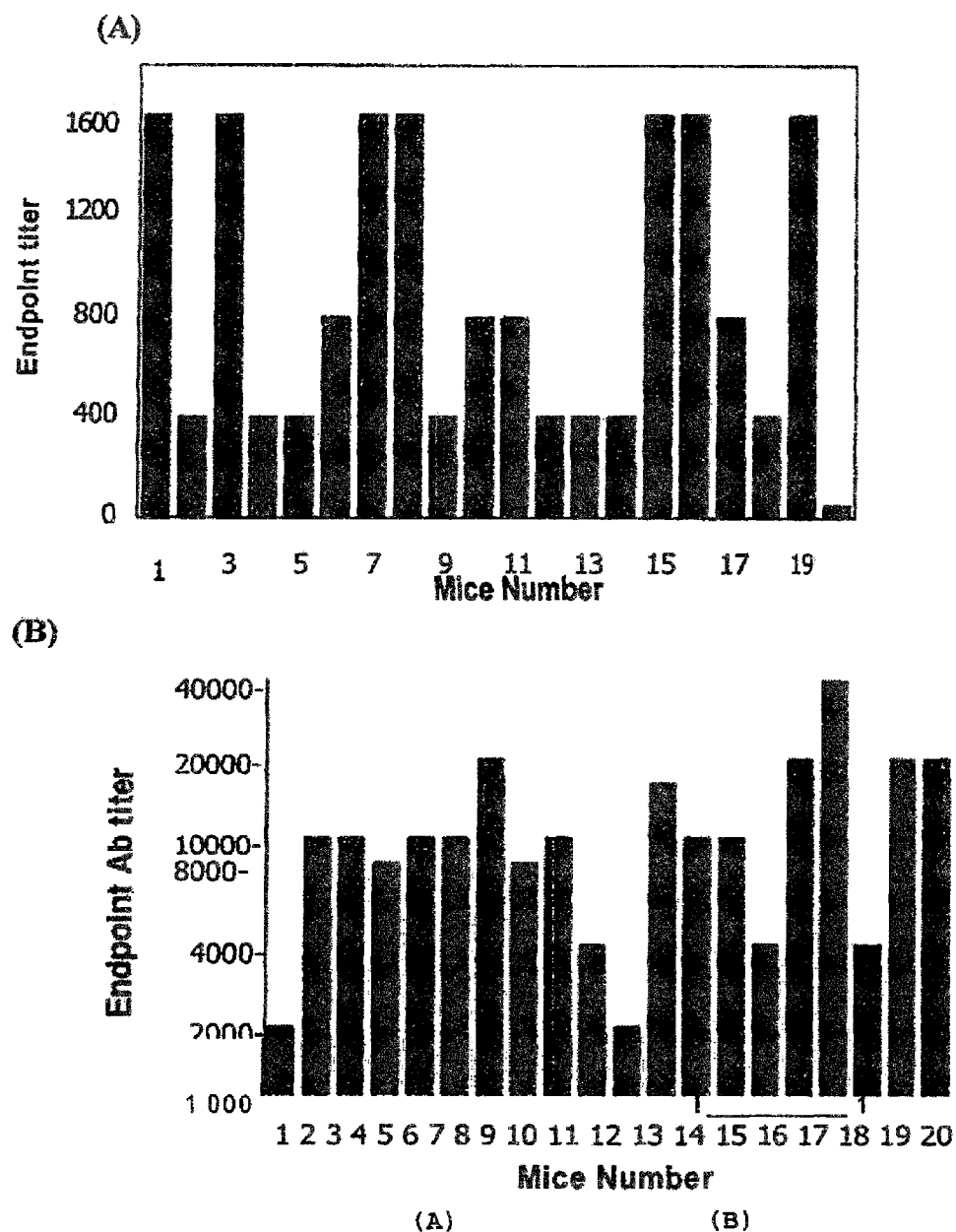
FIGURE 9 Immunogenecity Of The HAc DNA Vaccine (C)

FIGURE 10 Cell-Mediated Immunity Response Subsequent To CHA5 Immunization
(A)
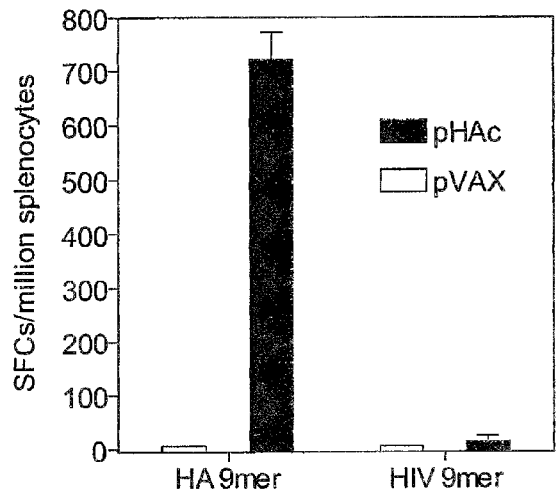
(B)
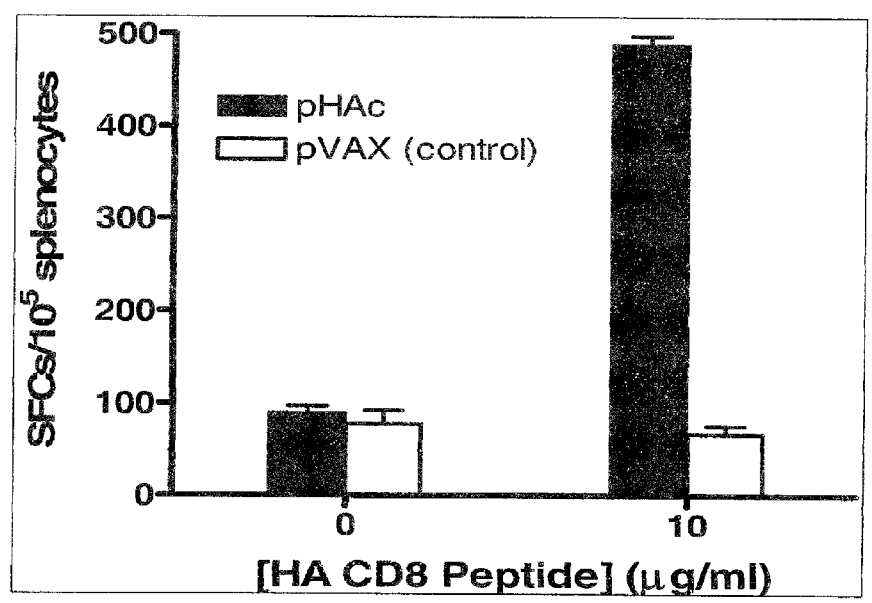

FIGURE 11 Vaccine – Induced Protection Against Lethal Viral Challenge
(A) One injection of the DNA vaccine
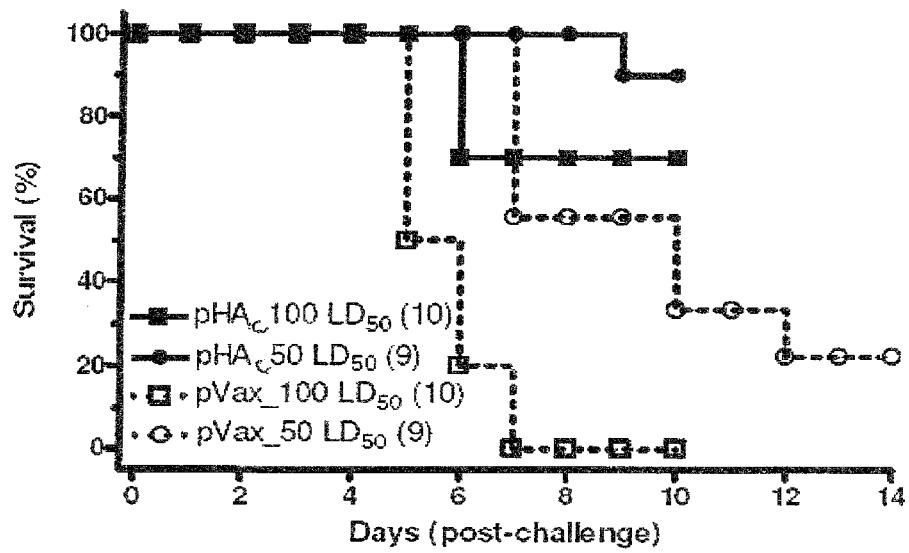
(B) Two injections of the DNA vaccine
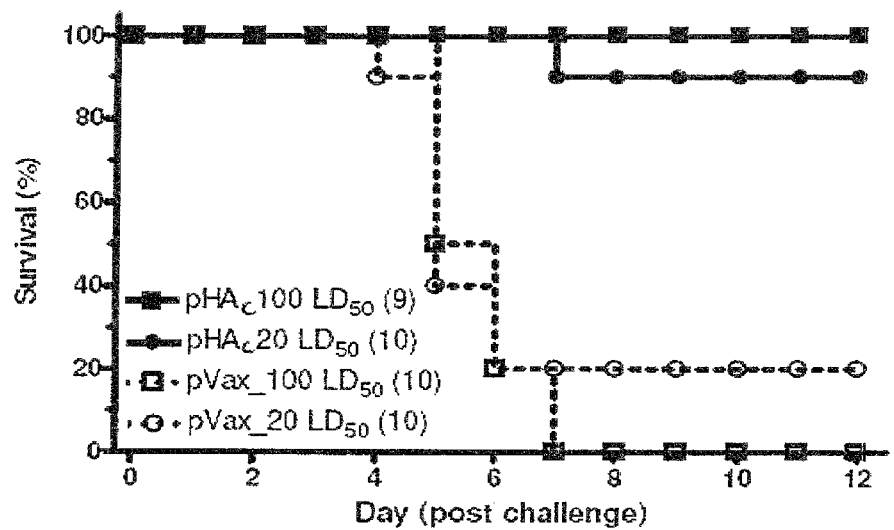

FIGURE 12A DNA VACCINE - INDUCED PROTECTION AGAINST VIRAL CHALLENGE
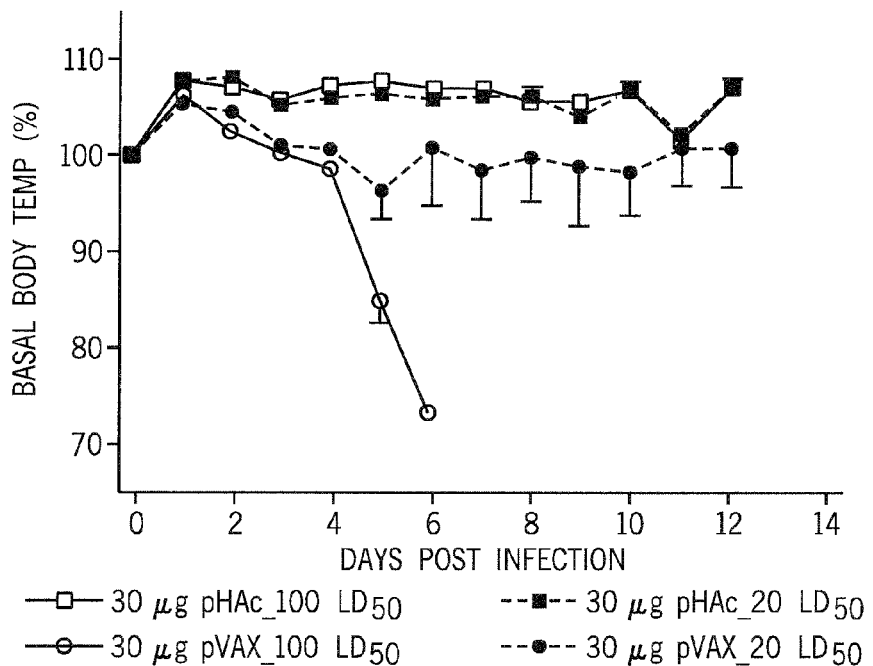
- □ 30 μg pHAc_100 LD$_{50}$
- ○ 30 μg pVAX_100 LD$_{50}$
- ■ 30 μg pHAc_20 LD$_{50}$
- ● 30 μg pVAX_20 LD$_{50}$
FIGURE 12B DNA VACCINE - INDUCED PROTECTION AGAINST VIRAL CHALLENGE
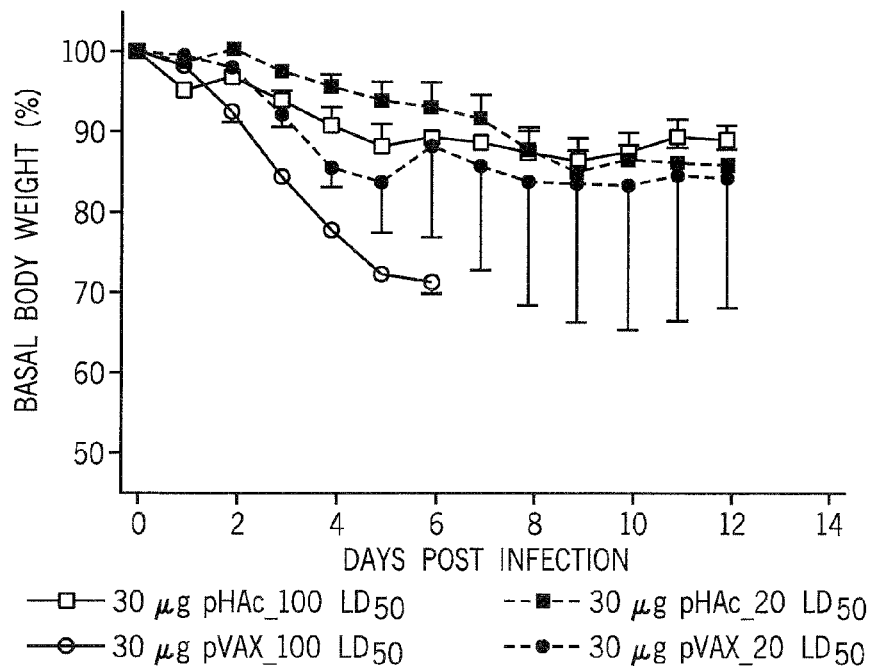
- □ 30 μg pHAc_100 LD$_{50}$
- ○ 30 μg pVAX_100 LD$_{50}$
- ■ 30 μg pHAc_20 LD$_{50}$
- ● 30 μg pVAX_20 LD$_{50}$

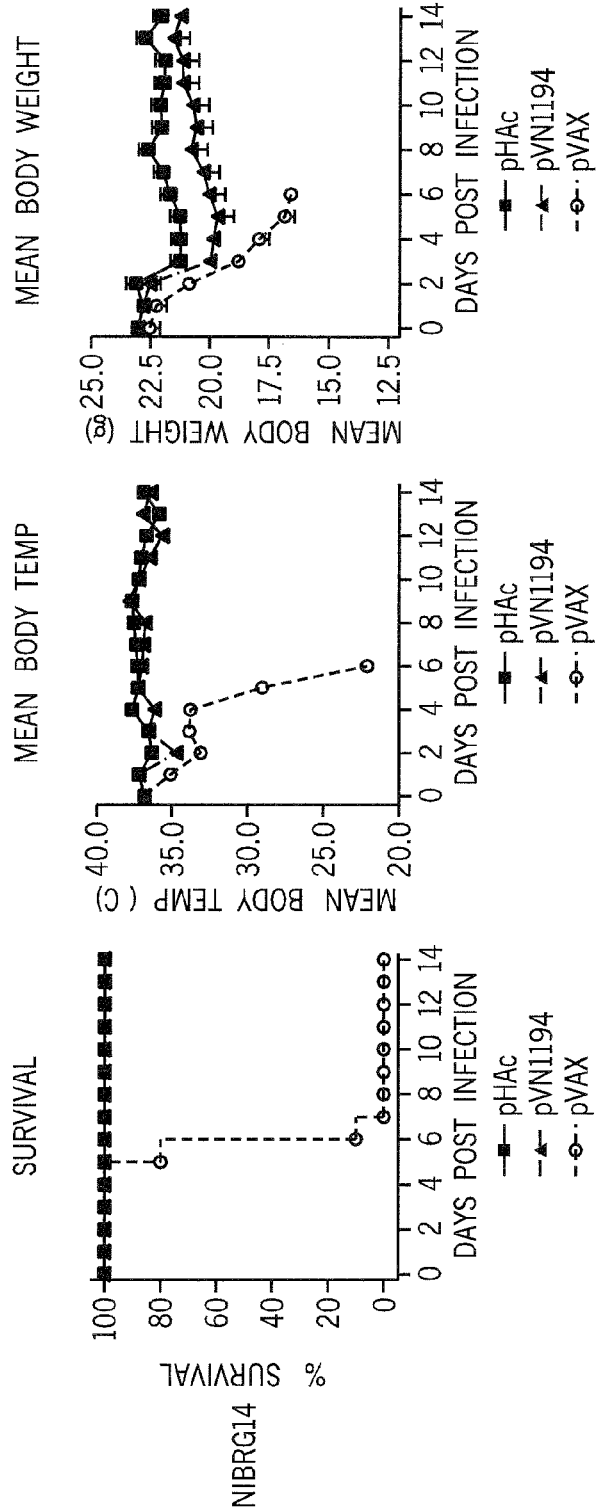
FIGURE 12C DNA VACCINE – INDUCED PROTECTION AGAINST VIRAL CHALLENGE

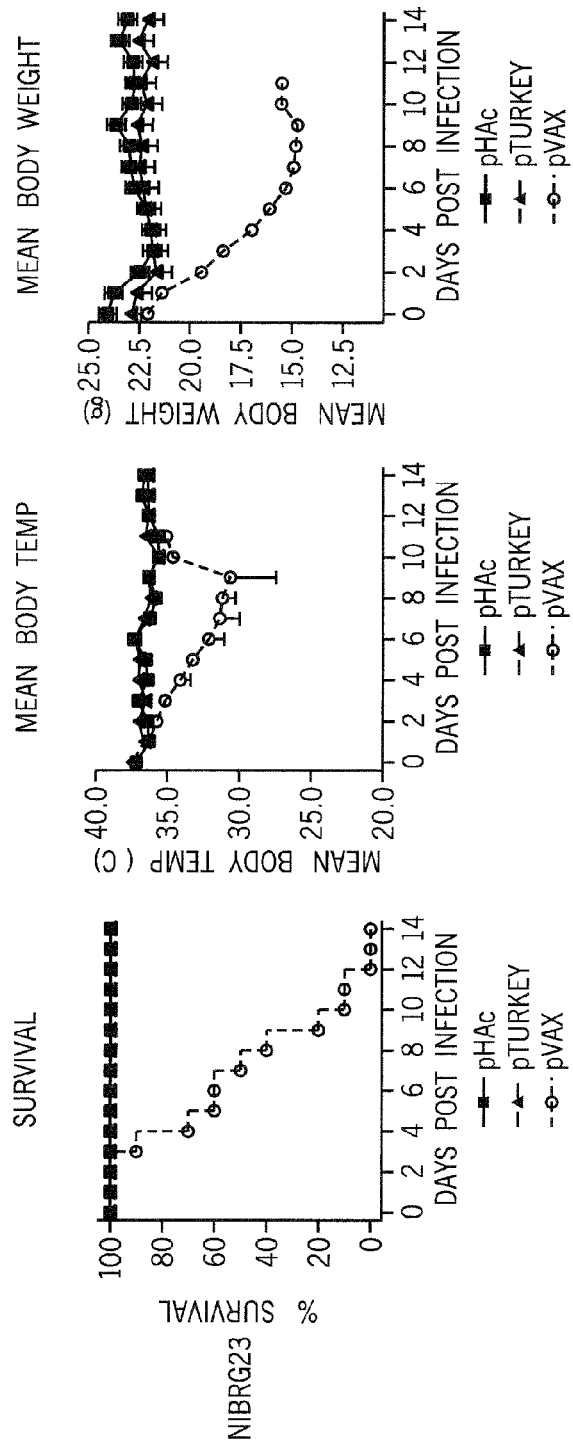
FIGURE 12D DNA VACCINE – INDUCED PROTECTION AGAINST VIRAL CHALLENGE

FIGURE 13A NEUTRALIZATION OF INFECTIVITY OF PSEUDOTYPED H5N1 VIRUSES

FIGURE 13B NEUTRALIZATION OF INFECTIVITY OF PSEUDOTYPED H5N1 VIRUSES pHAc
NT=4246

FIGURE 13C NEUTRALIZATION OF INFECTIVITY OF PSEUDOTYPED H5N1 VIRUSES pVN1203
NT=3572

FIGURE 13D NEUTRALIZATION OF INFECTIVITY OF PSEUDOTYPED H5N1 VIRUSES pVN1194
NT=1410

FIGURE 13E NEUTRALIZATION OF INFECTIVITY OF PSEUDOTYPED H5N1 VIRUSES pHK/213
NT=16857

FIGURE 13F NEUTRALIZATION OF INFECTIVITY OF PSEUDOTYPED H5N1 VIRUSES pID05
NT=276

FIGURE 13G NEUTRALIZATION OF INFECTIVITY OF PSEUDOTYPED H5N1 VIRUSES pID04
NT=2947

FIGURE 13H NEUTRALIZATION OF INFECTIVITY OF PSEUDOTYPED H5N1 VIRUSES pTURKEY
NT=1927

FIGURE 13I NEUTRALIZATION OF INFECTIVITY OF PSEUDOTYPED H5N1 VIRUSES pQINGHAI
NT=2021

FIGURE 13J NEUTRALIZATION OF INFECTIVITY OF PSEUDOTYPED H5N1 VIRUSES pE319-02
NT=809

FIGURE 13K NEUTRALIZATION OF INFECTIVITY OF PSEUDOTYPED H5N1 VIRUSES pFUJIAN
NT=2300

FIGURE 13L NEUTRALIZATION OF INFECTIVITY OF PSEUDOTYPED H5N1 VIRUSES pANHUI
NT = 175

FIGURE 13M NEUTRALIZATION OF INFECTIVITY OF PSEUDOTYPED H5N1 VIRUSES pVSVG
NT = NOT AVAILABLE

FIGURE 14 Relative Inhibition Of Hemadsorption of Chicken Red Blood Cells In The Presence Of HA Polypeptide Antisera FIGURE 15A IMPROVED RESISTANCE TO VIRAL CHALLENGE UTILIZING ALTERNATE-CLADE POLYNUCLEOTIDES
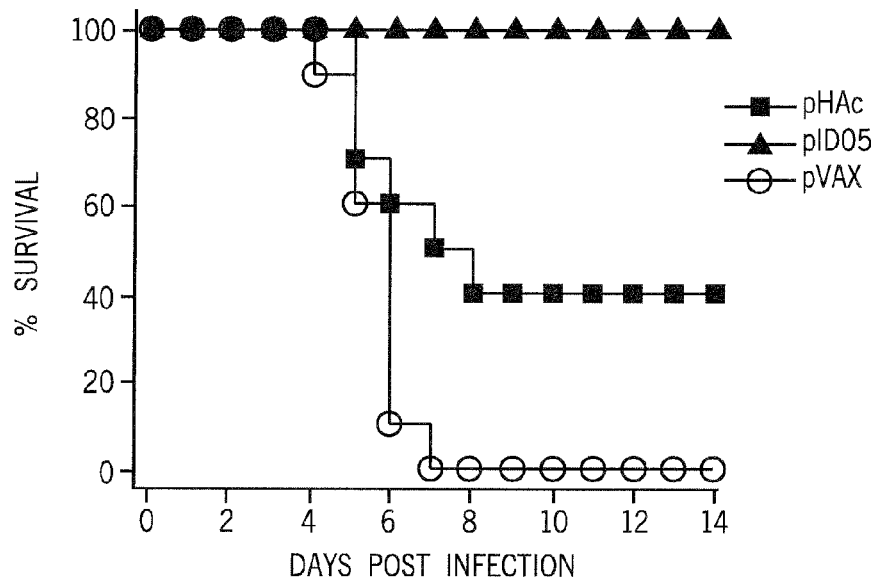
FIGURE 15B IMPROVED RESISTANCE TO VIRAL CHALLENGE UTILIZING ALTERNATE-CLADE POLYNUCLEOTIDES
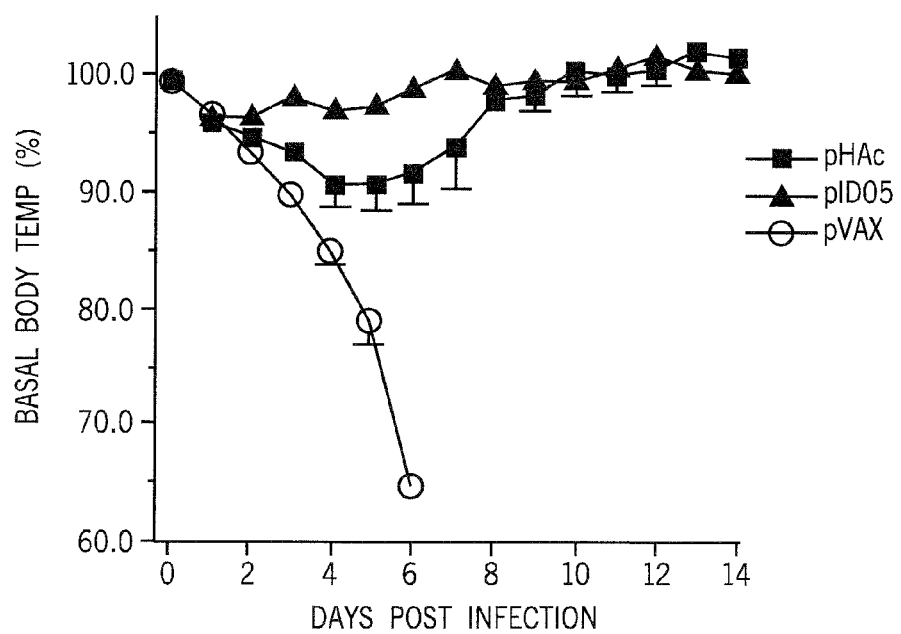

FIGURE 15C IMPROVED RESISTANCE TO VIRAL CHALLENGE UTILIZING ALTERNATE-CLADE POLYNUCLEOTIDES
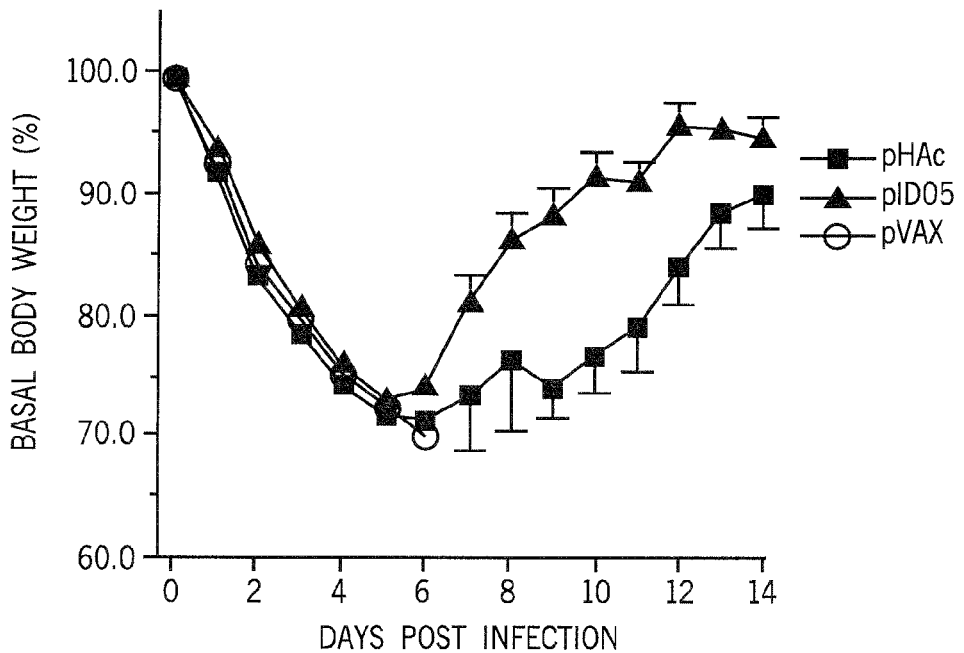
FIGURE 15D IMPROVED RESISTANCE TO VIRAL CHALLENGE UTILIZING ALTERNATE-CLADE POLYNUCLEOTIDES FIGURE 15E IMPROVED RESISTANCE TO VIRAL CHALLENGE UTILIZING ALTERNATE-CLADE POLYNUCLEOTIDES FIGURE 15F IMPROVED RESISTANCE TO VIRAL CHALLENGE UTILIZING ALTERNATE-CLADE POLYNUCLEOTIDES FIGURE 15G IMPROVED RESISTANCE TO VIRAL CHALLENGE UTILIZING ALTERNATE-CLADE POLYNUCLEOTIDES FIGURE 15H IMPROVED RESISTANCE TO VIRAL CHALLENGE UTILIZING ALTERNATE-CLADE POLYNUCLEOTIDES FIGURE 15I IMPROVED RESISTANCE TO VIRAL CHALLENGE UTILIZING ALTERNATE-CLADE POLYNUCLEOTIDES FIGURE 15J IMPROVED RESISTANCE TO VIRAL CHALLENGE UTILIZING ALTERNATE-CLADE POLYNUCLEOTIDES FIGURE 15K IMPROVED RESISTANCE TO VIRAL CHALLENGE UTILIZING ALTERNATE-CLADE POLYNUCLEOTIDES FIGURE 15L IMPROVED RESISTANCE TO VIRAL CHALLENGE UTILIZING ALTERNATE-CLADE POLYNUCLEOTIDES

FLU VACCINES AND METHODS OF USE THEREOF

RELATED APPLICATIONS

This nonprovisional patent application claims priority to U.S. Provisional Patent Application No. 60/897,062, filed on Jan. 24, 2007, which provisional patent application is hereby incorporated by reference in its entirety.

SEQUENCE LISTING

This application contains a sequence listing, submitted in both paper and a Computer Readable Form (CRF) and filed electronically via EFS. The electronic file is called "AcademiaSinica-030801-Sequence-ST25.txt" that is 22,147 bytes in size (measured in Windows XP) and created on Oct. 9, 2008.

FIELD OF THE INVENTION

The present disclosure relates to influenza hemagglutinin peptides, nucleotides encoding and methods of generating same. The present disclosure also relates to compositions, vaccines, therapeutics, and methods of use in inhibiting influenza infection and viral spread of single-clade and reassortant influenza virus.

BACKGROUND OF THE INVENTION

There has been a recent emergence of highly pathogenic avian influenza (HPAI) viral strains in poultry and their subsequent transmission to humans in southeast Asia, which has raised concerns about the potential pandemic spread of lethal disease. In 1997, highly pathogenic avian influenza H5N1 influenza virus was transmitted from poultry to humans in Hong Kong, resulting in eighteen infected people and six deaths, and reemerged in 2003 causing two similar cases with one fatality. H5N1 influenza virus infections in family clusters have raised the additional possibility of human-to-human transmission. As human exposure to and infection with H5N1 influenza viruses continues to increase, so, too, does the likelihood of the generation of an avian-human reassortant virus that may be transmitted efficiently within the global human population, which currently lacks H5N1 specific immunity. Such reassortant events between avian-human and swine-human influenza A viruses have been associated with at least the 1957 and 1968 influenza pandemics and potentially the 1918 pandemic. Concern over the potential for the generation of a pandemic H5 strain and its concomitant morbidity and mortality are spurring the search for an effective vaccine.

Influenza viruses are RNA orthomyxoviruses and consist of three types, A, B, and C. Influenza A viruses infect a wide variety of birds and mammals, including humans, horses, pigs, ferrets, and chickens. Influenza B and C are present only in humans. Animals infected with influenza A often act as a reservoir for the influenza virus, by generating pools of genetically and antigenically diverse viruses which are transmitted to the human population. Transmission may occur through close contact between humans and the infected animals, for example, by the handling of livestock. Transmission from human to human may occur through close contact, or through inhalation of droplets produced by coughing or sneezing.

The outer surface of the influenza A virus particle consists of a lipid envelope which contains the glycoproteins hemagglutinin (HA) and neuraminidase (NA). The HA glycoprotein is comprised of two subunits, termed HA1 and HA2. HA contains a sialic acid binding site, which binds to sialic acid found on the outer membrane of epithelial cells of the upper and lower respiratory tract, and is absorbed into the cell via receptor mediated endocytosis. Once inside the cell, the influenza virus particle releases its genome, which enters the cell nucleus and initiates production of new influenza virus particles.

NA is also produced, which cleaves sialic acid from the surface of the cell to prevent recapture of released influenza virus particles. The virus incubates for a short period, roughly five days in a typical case, although the incubation period can vary greatly. Virus is secreted by affected cells approximately one day prior to the onset of the illness, and the resultant illness typically lasts three to five days. Typical symptoms include fever, fatigue, malaise, headache, aches and pains, coughing, and sore throat. Some symptoms may persist for several weeks post infection.

Different strains of influenza virus are characterized primarily by mutations in the HA and NA glycoproteins, and thus HA and NA identity are used to identify viral subtypes (i.e., H5N1 indicates HA subtype 5 and NA subtype 1). Influenza vaccines often target the HA and NA molecules. Conventional influenza virus vaccines often utilize whole inactivated viruses, which present the appropriate HA and/or NA molecules as antigens to prime the cellular and humoral immune systems. Alternatively, recombinant forms of the HA and NA proteins or their subunits have been used as vaccines. However, influenza is an RNA virus and is thus subject to frequent mutation, resulting in constant and permanent changes to the antigenic composition of the virus. In one example, small, minor changes to the antigenic composition are often referred to as antigenic drift. In another example, Influenza A viruses are also capable of "swapping" genetic materials from other subtypes in a process called reassortment, resulting in a major change to the antigenic composition of the virus. Because the immune response against the viral particles relies upon the binding of antibodies to and cell-mediated immune system component recognition of the HA and NA glycoproteins, frequent changes to the composition and structure of glycoproteins reduces the effectiveness of the humoral and cell-based immune responses against influenza viruses over time, eventually leading to a lack of immunity. The ability of influenza A to undergo a rapid antigenic shift can often trigger influenza epidemics due to this lack of preexisting immunity to the new strain.

The lengthy development time and limited production capability of conventional inactivated influenza vaccines could severely hinder the ability to control the pandemic spread of avian influenza through vaccination. Thus, there is a need in the art for a method of quickly developing and mass producing large quantities influenza vaccine.

SUMMARY OF THE INVENTION

In one embodiment, the isolated polynucleotide composition comprises a nucleic acid sequence corresponding to or homologous to SEQ ID. NO.: 2.

In another embodiment, the isolated polynucleotide composition further encodes a cytokine or growth factor.

In another embodiment, the isolated polynucleotide composition further comprises a cytokine, a growth factor, an antiviral, an adjuvant, an excipient, or a combination thereof.

In another embodiment, the isolated polynucleotide encodes a polypeptide comprising an amino acid sequence corresponding to, or homologous to that set forth in SEQ. ID. NO: 1.

In another embodiment, the polypeptide is at least partially glycosylated.

In another embodiment, an antibody to the polypeptide is disclosed

In another embodiment, an oligonucleotide specifically hybridizing with the isolated polynucleotide is disclosed.

In another embodiment, the oligonucleotide exhibits greater affinity for the isolated polynucleotide, as compared to a polynucleotide comprising a wild type influenza sequence.

In another embodiment, the isolated polynucleotide composition further comprises a vector.

In another embodiment, the composition further encompasses a polynucleotide encoding a cytokine or growth factor.

In another embodiment, the codons of the composition are optimized for mammalian expression.

In another embodiment, the composition comprises at least one nucleic acid sequence corresponding to or homologous to at least one of SEQ ID. NO.: 2, 4, and/or 6.

In another embodiment, the composition comprising at least one nucleic acid sequence corresponding to or homologous to at least one of SEQ ID. NO.: 2, 4, and/or 6 further encodes a cytokine or growth factor.

In another embodiment, the composition comprising at least one nucleic acid sequence corresponding to or homologous to at least one of SEQ ID. NO.: 2, 4, and/or 6 further comprises a cytokine, a growth factor, an antiviral, an adjuvant, an excipient, or a combination thereof.

In another embodiment, the composition comprising at least one nucleic acid sequence corresponding to or homologous to at least one of SEQ ID. NO.: 2, 4, and/or 6 encodes a polypeptide comprising an amino acid sequence corresponding to, or homologous to that set forth in at least one of SEQ. ID. NOs: 1, 3, and/or 5.

In another embodiment, the composition comprising at least one nucleic acid sequence corresponding to or homologous to at least one of SEQ ID. NO.: 2, 4, and/or 6 encodes a polypeptide that is subsequently at least partially glycosylated.

In another embodiment, the polypeptide comprising an amino acid sequence corresponding to, or homologous to that set forth in at least one of SEQ. ID. NOs: 1, 3, and/or 5 produces an antibody to at least one of the polypeptides corresponding to, or homologous to that set forth in at least one of SEQ. ID. NOs: 1, 3, and/or 5.

In another embodiment, an oligonucleotide specifically hybridizes to at least one nucleic acid sequence corresponding to or homologous to at least one of SEQ. ID. NO.: 2, 4, and/or 6

In another embodiment, the oligonucleotide of the preceding paragraph, wherein said oligonucleotide exhibits greater affinity for at least one nucleic acid sequence corresponding to or homologous to at least one of SEQ ID. NO.: 2, 4, and/or 6, as compared to a polynucleotide comprising a wild type influenza sequence.

In another embodiment, the composition comprising at least one nucleic acid sequence corresponding to or homologous to at least one of SEQ ID. NO.: 2, 4, and/or 6 is a vector.

In another embodiment, the composition comprising at least one nucleic acid sequence corresponding to or homologous to at least one of SEQ ID. NO.: 2, 4, and/or 6 further encloses a polynucleotide encoding a cytokine or growth factor.

In another embodiment, the composition comprising at least one nucleic acid sequence corresponding to or homologous to at least one of SEQ ID. NO.: 2, 4, and/or 6 includes codons that are optimized for mammalian expression.

In another embodiment, a method is disclosed comprising:
Administering a sufficient amount of at least one isolated polynucleotide selected from at least one of the group consisting of isolated polynucleotides corresponding to, or homologous to, SEQ. IDs NOs. 2, 4, and/or 6 to a subject;
Wherein the subject is capable of resisting subsequent viral challenge.

In another embodiment, the amount of antibody titer specific to viral antigens produced by the subject subsequent to viral challenge is increased by at least 2% as compared to the amount of antibody titer specific to viral antigens produced by a virally-challenged subject that was not administered an isolated polynucleotide corresponding to, or homologous to, SEQ. IDs NOs. 2, 4, and/or 6.

In another embodiment, the amount of interferon-γ produced by CD8-positive cells of the subject subsequent to viral challenge is increased by at least 2% as compared to the amount interferon-γ produced by a virally-challenged subject that was not administered an isolated polynucleotide corresponding to, or homologous to, SEQ. IDs NOs. 2, 4, and/or 6.

In another embodiment, the amount of chicken red blood cell hemadsorption by challenge virus in solution with subject serum is reduced by at least 2% as compared to amount of chicken red blood cell hemadsorption of virally-challenged subject that was not administered an isolated polynucleotide of an isolated polynucleotide comprising a nucleic acid sequence corresponding to or homologous to SEQ ID NO:2, wherein the codons are optimized for mammalian expression.

In another embodiment, the post-challenge body temperature of the subject is maintained within 2% of the body temperature of the subject pre-challenge.

In another embodiment, the post-challenge weight loss of a subject is at least 2% less as compared to the post-challenge weight loss of virally-challenged subject that was not administered an isolated polynucleotide of an isolated polynucleotide comprising a nucleic acid sequence corresponding to or homologous to SEQ ID NO:2, wherein the codons are optimized for mammalian expression.

In another embodiment, the post-challenge survivability of a subject is improved as compared to a virally-challenged subject that was not administered an isolated polypeptide of an isolated polynucleotide comprising a nucleic acid sequence corresponding to or homologous to SEQ ID NO:2, wherein the codons are optimized for mammalian expression.

In another embodiment, the subsequent viral challenge is an influenza virus strain H5N1.

In another embodiment, the subsequent viral challenge is an influenza viral strain that is the product of viral reassortant.

In another embodiment, the subject is capable of resisting subsequent viral challenge with an influenza virus of an alternative clade or sub-clade than the initial viral challenge.

BRIEF DESCRIPTION OF THE DRAWINGS

FIG. 1 depicts a phylogenetic analysis of the consensus HA sequence versus the HA of WHO H5N1 vaccine strains. According to WHO definition, the circulating H5N1 viruses can separate to two clades. The consensus HA nucleotide sequence is designated as HAc, and a plasmid construct encompassing the consensus HAc nucleotide sequence is designated as pHAc, for purposes of this application. The consensus HA nucleotide sequence (blue character) (designated as "Consensus (HAc)") phylogenetically resides between WHO—suggested vaccine strains (red character) (08 Indonesia/5/2005 (NIBRG-2); 010 turkey/Turkey/1/2005 (NIBRG-23); 011 ws/Mongolia/244/2005; 012 bhg/Qinghai/1A/2005; 014 Anhui/1/2005) in clade 1 and clade 2 of the H5N1 influenza viral family. The star marks the influenza A viruses that are available for virus challenge experiments.

FIG. 2 depicts the protein (amino acid) sequence of the consensus hemagglutinin (HA) (SEQ ID NO: 1) coded for by the HAc consensus polynucleotide (SEQ ID NO:2).

FIG. 3 depicts the HAc nucleotide (base) sequence (SEQ ID NO: 2) coding for the consensus HA of FIG. 2 (SEQ ID NO: 1).

FIG. 4 depicts the protein (amino acid) sequence of a HA related to H5N1 viral family subclade 2.1 (H5 of RG2; reassortant of H5N1 virus strain Indonesia/5/2005) of the H5N1 influenza viral clade (SEQ ID NO: 3), coded for by the optimized polynucleotide sequence (pID50) of SEQ ID NO: 4 (FIG. 5) and designated "ID5".

FIG. 5 depicts the optimized nucleotide (base) sequence (SEQ ID NO: 4) (ID5) coding for the HA related to clade 2.1 listed in SEQ ID NO: 3.

FIG. 6 depicts the protein (amino acid) sequence of a HA related to H5N1 viral family subclade 2.3 (H5 of RG5; Anhui/01/2005(H5N1)/PR8-IBCDC-RG5) of the H5N1 influenza viral clade (SEQ ID NO: 5) coded for by the optimized polynucleotide sequence (pAnhui) of SEQ ID NO:6 (FIG. 7) and designated "Anhui"

FIG. 7 depicts the optimized nucleotide (base) sequence (SEQ ID NO:6)("Anhui") coding for the HA related to clade 2.3 listed in SEQ ID NO: 5.

FIG. 8 demonstrates the characterization of the HAc DNA vaccine. HEK293 cells were transfected with individual plasmids encoding HA genes of different H5N1 strains. The cell lysates were then analyzed by immunoblotting with anti-HA polyclonal antibodies.

FIG. 8(A) is a photograph of the immunoblot depicting relative expression of the HA consensus sequence viral protein coded for by SEQ IDs no 1 and 2, as assayed by immunoblot The virus strains are shown on the top of each lane. HAc: the consensus HA, VN 1203: VN 1203/2004, VN1194: VN1194/2004, TS: dk/China/E319-2/03, QH: bhg/QingHai/62/2005, HK: 11K/213/03, ID: ck/Indonesia/5/2004, FJ: dk/Fujian/1734/05, pVAX: empty plasmid control. As a photograph of an immunological blot, FIG. 8(A) is not capable of being illustrated in an ink drawing and/or is shown more clearly in a photograph.

FIG. 8 (B) depicts relative hemadsorption of chicken red blood cells by HAc—transfected and resultant HA polypeptide—expressing HEK293 cells. The HEK293 cells were transfected with individual plasmids encoding HA genes of different H5N1 strains (including pHAc) and then the cells were incubated with chicken red blood cells for 30 minutes. The amount of absorbed red blood cells was analyzed by the amount of hemoglobin, which can be detected by optical absorbance at 540 nm. Shown on the bottom of each bar represents the virus strains, same as above FIG. 9 demonstrates the immunogeneicity of the consensus HAc polynucleotide vaccine.

FIG. 9 (B) depicts endpoint antibody titer assayed subsequent to two injections of HAc polynucleotide vaccine spaced three weeks apart. The mice were immunized with two injections of 30 μg of pHAc at a three-week interval. Sera were collected at two weeks after the second injection. The endpoint antibody titer was determined using ELISA against the consensus HA-hFc fusion protein.

FIG. 9(C) demonstrates the difference in antibody titer resulting from immunization with control plasmid (pVAX) or with pHAc plasmid. Balb/c mice were vaccinated with 30 μg pHAc or with pVAX (control) plasmid via electroporation at days 1 and 21. As indicated by FIG. 9(C), the antibody titer of the mice immunized with pHAc was considerably higher than the antibody titer of the mice immunized with pVAX.

FIG. 10 quantitates the cell-mediated immunity induced by the DNA vaccine. FIG. 10(A) illustrates the increase in IFN-γ released by CD8-positive T cells in response to vaccination of a subject with consensus pHAc polynucleotide sequence and subsequent introduction of HA via viral challenge. Splenocytes were obtained from a subject that was immunized with consensus HAc polynucleotide sequence and in vitro stimulated with an HA-specific CD8-responsive peptide (HA 9mer) or an irrelevant peptide (HIV 9mer). FIG. 10A illustrates the increase in IFN-γ released by CD8-positive T cells in response to an in vitro stimulation of HA peptide (HA 9mer), indicating the induction of the cell-mediated immunity by the HAc nucleotide vaccine.

FIG. 10(B) further illustrates cellular immunity responses subsequent to HAc polynucleotide immunization. In FIG. 10(B), viral challenge of mouse splenocytes with HA—expressing viruses post—immunization with HAc nucleotide vaccine (in this instance, pHAc) resulted in a robust cell-mediated immune response, shown by an increase in IFN-γ released by CD8-positive T cells and assayed via ELIspot.

FIG. 11 plots HAc DNA vaccine—induced protection against challenge with a lethal dose of NIBRG-14 (a representative H5N1 clade 1 avian flu virus). In FIG. 11 (A), mice were immunized with one injection of the consensus HAc vaccine (in this instance, pHAc) or the control plasmid expression vector (pVax) followed with viral challenge using 50 or 100 fold of the established $LD_{50}$ of NIBRG-14. The numbers in the parentheses indicated the number of mice used in each group. In FIG. 11 (B), mice were immunized with two injections of the HAc DNA vaccine or the control plasmid expression vector (pVax) followed with virus challenge as in FIG. 11(A). As shown in FIGS. 11(A) and (B), immunization with pHAc polynucleotide vaccine prior to viral challenge resulted in an increased rate of survival.

FIG. 12 plots changes in body temperature (A) and body weight (B) of mice challenged with lethal doses of NIBRG-14 (a representative H5N1 clade 1 avian flu virus). Mice were immunized with two injections of the HAc DNA vaccine (in this instance, pHAc) or the control plasmid expression vector (pVax) and then challenged with NIBRG-14 at 20 and 100 fold of the established $LD_{50}$ of the virus.

FIG. 12A demonstrates that mice immunized with HAc polynucleotide (in this instance, pHAc) were able to maintain a higher, more stable basal body temperature over time than those immunized with the control plasmid vector.

FIG. 12B demonstrates that mice immunized with HAc polynucleotide (in this instance, pHAc) were able to maintain a higher average body weight (and to lose a lesser percentage of body weight) over time than those immunized with the control plasmid vector.

FIGS. 12C-12D further demonstrate the ability of HAc DNA vaccination to confer improved resistance to viral challenges by reassortant H5N1 influenza viruses including NIBRG14 (a representative H5N1 clade 1 avian influenza virus) and NIBRG23 (a representative H5N1 clade 2 avian influenza virus). As shown in FIGS. 12C-12D, vaccination with HAc polynucleotide (in this instance, pHAc) resulted in improved survival, increased body weight, and increased temperature as compared to pVAX-vaccinated subjects challenged with the NIBRG14 (FIG. 12C and NIBRG23 (FIG.

Figure 9:
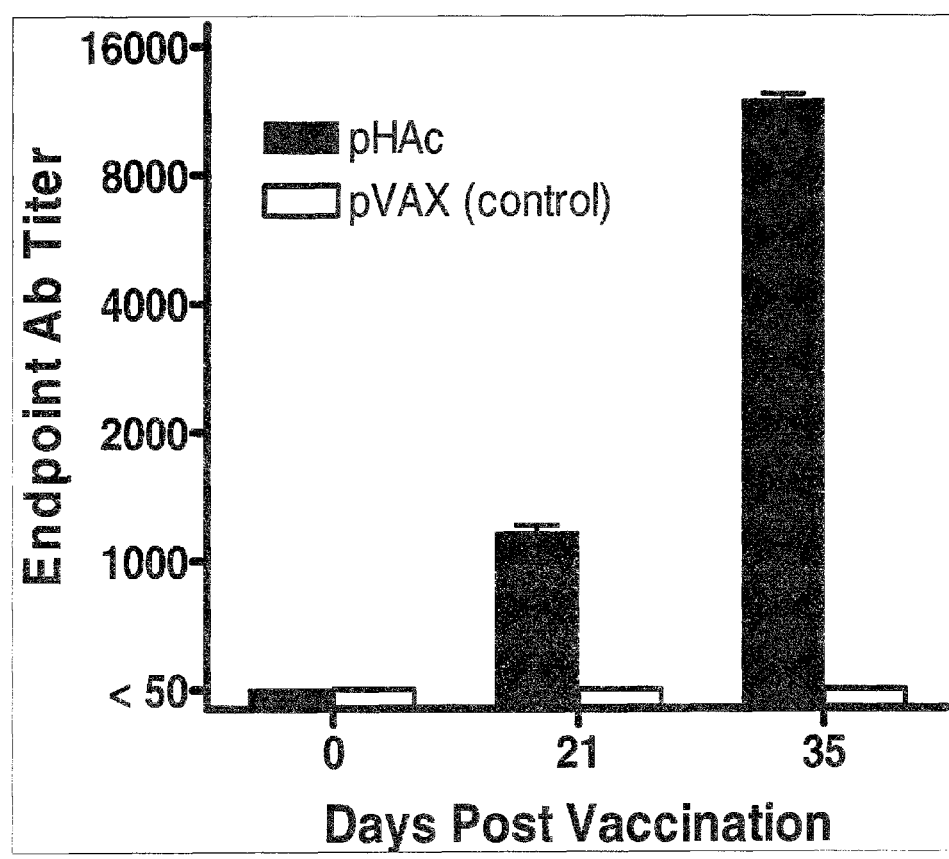
In FIG. 9 (A), the mice were immunized with one injection containing 30 μg of pHAc and serum were collected after three weeks. The endpoint serum antibody titer was determined using ELISA against the consensus HA-hFc fusion protein.

12D) influenza viruses, as well as compared to vaccination with a homologous isolated polynucleotide coding for HA (pVN 1194).

FIG. 13A demonstrates neutralization of infectivity of pseudotyped H5N1 viruses on MDCK cells by immune serum obtained from mice 2 weeks after a 2$^{nd}$ immunization with HAc DNA vaccine (in this instance, pHAc). The HA-pseudotyped viruses generated comprised an HIV backbone and HA of different H5N1 virus strains, as described. As shown, immunization with pHAc polynucleotide vaccine resulted in broad-based immunity against viral challenge from a variety of H5 protein—expressing pseudotype viruses.

FIGS. 13B-13M demonstrate neutralization of infectivity of HA-pseudotyped viruses by anti-sera obtained from mice receiving two injections of HAc polynucleotide vaccine. Prior to infection of MDCK cells, HA-HIV pseudoviruses were preincubated with antisera at the indicated serum dilution. Data were collected from subsequent infection with a variety of preincubated HA-HIV pseudoviruses.

FIG. 14 depicts relative inhibition of hemadsorption of chicken red blood cells by HA in the presence of antisera raised against HA polypeptides encoded by the HAc nucleotide. HA-expressing cells were incubated with red blood cells in the presence (empty bar) or absence (black bar) of antisera raised against consensus HA polypeptides encoded by the HAc polynucleotide. The associated red blood cells were then quantitated using optical density measurements of the amount of hemoglobin. The values detected without antisera incubation were used as 100% in order to calculate the inhibition of antisera raised against consensus HA polypeptides encoded by the HAc polynucleotide. Again, broad-based inhibition of hemadsorption across diverse HA-expressing viral clades is seen.

FIG. 15 depicts improved resistance to viral challenge by utilizing specific alternate-clade DNA vaccines. In FIGS. 15A-15F, immunization of Balb/c mice with two injections of HAc nucleotide (in this example via pHAc) and with the HA nucleotide sequence of FIG. 5 (ID5) (in this example via pID5) encoding the sequences of FIG. 5 was followed by viral challenge with reassortant RG2 virus representing clade 2.1 H5N1. As compared to both control pVAX and pHAc, vaccination with pID5 yielded increased survival and maintenance of body weight and body temperature in the studied population. In FIGS. 15G-15L, immunization of Balb/c mice with two injections of HAc (in this instance via pHAc) and with the HA nucleotide sequence of FIG. 7 (Anhui) (in this instance via pAnhui) was followed by viral challenge with reassortant RG5 virus representing clade 2.3 H5N1. As compared to both control pVAX and pHAc, vaccination with pAnhui yielded increased maintenance of body weight and body temperature in the studied population.

DETAILED DESCRIPTION OF THE PRESENT INVENTION

In the following detailed description, numerous specific details are set forth in order to provide a thorough understanding of the disclosure. However, it will be understood by those skilled in the art that the present disclosure may be practiced without these specific details. In other instances, well-known methods, procedures, and components have not been described in detail so as not to obscure the present disclosure.

For the purposes of describing the present disclosure, the following terms are intended to refer to the associated definitions as described below:

"Adjuvant" means any pharmacological or immunological agent capable of modifying the effect of other agents (e.g., drugs, vaccines) while having few if any direct effects when given by themselves. In this sense, they are roughly analogous to chemical catalysts. Types of adjuvants include, but are not limited to, pharmaceutical adjuvants; immunologic adjuvant; and/or adjuvant chemotherapy. Pharmaceutical adjuvants are drugs that have few or no pharmacological effects by themselves, but may increase the efficacy or potency of other drugs when given at the same time Immunological adjuvants include agents that may stimulate the immune system and increase the response to a vaccine, without having any specific antigenic effect in itself. Known adjuvants include, but are not limited to, oils, aluminum salts and virosomes.

"Administering" means in vitro or in vivo administration, wherein in vivo administration may encompass oral, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into the body.

"Amino Acid" means a set of chemical entities including at least the 20 naturally occurring amino acids; those amino acids often modified post-translationally in vivo, including for example hydroxyproline, phosphoserine and phosphothreonine; and other unusual amino acids including, but not limited to, 2-aminoadipie acid, hydroxylysine, isodesmosine, norvaline, nor-leucine and ornithine. Furthermore, the term "amino acid" includes both D- and L-amino acids.

"Anhui" means a polynucleotide of the H5N1 influenza family encoding a hemagglutinin polypeptide and having the following base pair sequence:

```
                                        (SEQ ID NO: 6)
ATG GAG AAG ATC GTG CTG CTG CTC GCC ATC GTG AGC

CTG GTG AAG AGC GAC CAG ATC TGC ATC GGA TCC CAC

GCC AAC AAC AGC ACC GAG CAG GTG GAC ACC ATC ATG

GAG AAG AAC GTG ACC GTG ACC CAC GCC CAG GAC ATC

CTG GAG AAG ACC CAC AAC GGC AAG CTG TGC GAC CTG

GAC GGC GTG AAG CCT CTG ATC CTG AGA GAC TGC AGC

GTG GCC GGC TGG CTG CTG GGC AAC CCT ATG TGC GAC

GAG TTC ATC AAC GTG CCT GAG TGG AGC TAC ATC GTG

GAG AAG GCC AAC CCT GCC AAC GAC CTG TGC TAC CCT

GGC AAC TTC AAC GAC TAC GAG GAG CTG AAG CAC CTG

CTG AGC AGA ATC AAC CAC TTC GAG AAG ATC CAG ATC

ATC CCT AAG AGC AGC TGG AGC GAC CAC GAG GCC AGC

AGC GGC GTG AGC AGC GCC TGC CCT TAC CAG GGC ACG

CCC AGC TTC TTC AGA AAC GTG GTG TGG CTG ATC AAG

AAG AAC AAC ACC TAC CCT ACC ATC AAG AGA AGC TAC

AAC AAC ACC AAC CAG GAG GAC CTG CTG ATC CTG TGG

GGC ATC CAC CAC TCT AAC GAC GCC GCC GAG CAG ACC

AAG CTG TAC CAG AAC CCT ACC ACC TAC ATC AGC GTG
```

-continued

GGC ACC AGC ACC CTG AAC CAG AGA CTG GTG CCT AAG

ATC GCC ACC AGA AGC AAG GTG AAC GGC CAG AGC GGC

AGA ATG GAC TTC TTC TGG ACC ATC CTG AAG CCT AAC

GAC GCC ATC AAC TTC GAG AGC AAC GGC AAC TTC ATC

GCC CCT GAG TAC GCC TAC AAG ATC GTG AAG AAA GGC

GAC AGC GCC ATC ATG AAG AGC GAG GTG GAG TAC GGCAAC

TGC AAC ACC ATG TGC CAG ACC CCT ATC GGC GCC ATC

AAC AGC AGC ATG CCT TTC CAC AAC ATC CAC CCT CTG

ACC ATC GGC GAG TGC CCT AAG TAC GTG AAG AGC AAC

AAA CTG GTG CTG GCC ACC GGC CTG AGA AAC AGC CCT

CTG AGA GAG AGA AGA AGA AAG AGA GGC CTG TTC GGC

GCC ATC GCC GGC TTC ATC GAG GGC GGC TGG CAG GGC

ATG GTG GAC GGC TGG TACGGC TAC CAC CAC AGC AAC

GAG CAG GGC AGC GGC TAC GCC GCC GAC AAGGAG AGC

ACC CAG AAG GCC ATC GAC GGC GTG ACC AAC AAG GTG

AAC AGCATC ATC GAC AAG ATG AAC ACC CAG TTC GAG

GCC GTG GGC AGA GAG TTCAAC AAC CTG GAG AGA AGA

ATC GAG AAC CTG AAC AAG AAG ATG GAG GACGGC TTC

CTG GAC GTG TGG ACC TAC AAC GCC GAG CTG CTG GTG

CTG ATGGAG AAC GAG AGA ACC CTG GAC TTC CAC GAC

AGC AAC GTG AAG AAC CTGTAC GAC AAG GTG AGA CTG

CAG CTG AGA GAC AAC GCC AAG GAG CTG GGCAAC GGC

TGC TTC GAG TTC TAC CAC AAG TGC GAC AAC GAG TGC

ATG GAGAGC GTG AGA AAC GGC ACC TAC GAC TAC CCT

CAG TAC AGC GAG GAG GCCAGA CTG AAG AGA GAG GAG

ATC AGC GGC GTG AAG CTG GAG AGC ATC GGCACC TAC

CAG ATC CTG AGC ATC TAC AGC ACC GTG GCC AGC AGC

CTG GCCCTG GCC ATC ATG GTG GCC GGC CTG AGC CTG

TGG ATG TGC AGC AAC GGCAGC CTG CAG TGC AGA ATC

TGC ATC

Which polypeptide encodes the following amino acid sequence:

MEKIVLLLAIVSLVKSDQICIGSHANNSTEQVDT (SEQ ID NO: 7)

IMEKNVTVTHAQDILEKTHNGKLCDLDGVKPLIL

RDCSVAGWLLGNPMCDEFINVPEWSYIVEKANPA

NDLCYPGNFNDYEELKHLLSRINHFEKIQIIPKS

SWSDHEASSGVSSACPYQGTPSFFRNVVWLIKKN

NTYPTIKRSYNNTNQEDLLILWGIHHSNDAAEQT

KLYQNPTTYISVGTSTLNQRLVPKIATRSKVNGQ

SGRMDFFWTILKPNDAINFESNGNFIAPEYAYKI

-continued

VKKGDSAIMKSEVEYGNCNTMCQTPIGAINSSMP

FHNIHPLTIGECPKYVKSNKLVLATGLRNSPLRE

RRRKKRGLFGAIAGFIEGGWQGMVDGWYGYHHSN

EQGSGYAADKESTQKAIDGVTNKVNSIIDKMNTQ

FEAVGREFNNLERRIENLNKKMEDGFLDVWTYNA

ELLVLMENERTLDFHDSNVKNLYDKVRLQLRDNA

KELGNGCFEFYHKCDNECMESVRNGTYDYPQYSE

EARLKREEISGVKLESIGTYQILSIYSTVASSLA

LAIMVAGLSLWMCSNGSLQCRICI.

"Antigen" means a molecule capable of stimulating an immune response.

"Antigen Presenting Cell" means a cell that displays foreign antigen complexed with MHC on its surface. T-cells may recognize this complex using their T-cell receptor (TCR).

"Antiviral" means any of a class of molecules, substances or medications used specifically for treating viral infections. Like antibiotics, specific antivirals are used for specific viruses. Antiviral drugs are one class of antimicrobials, a larger group which also includes antibiotic, antifungal and antiparasitic drugs. They are relatively harmless to the host, and therefore can be used to treat infections.

"Cell-Based Immunity" means an immune response mediated through T cells and related cell types "Clade" means a taxonomic group of organisms comprising a single common ancestor and all the descendants of that ancestor. Any such group is considered to be a monophyletic group of organisms, and can be represented by both a phylogenetic analysis, as in a tree diagram, and by a cladogram (see cladistics), or simply as a taxonomic reference "Cluster of Differentiation" or "CD" means a protocol used for the identification and investigation of cell surface molecules present on leukocytes. CD molecules can act in numerous ways, often acting as receptors or ligands (the molecule that activates a receptor) important to the cell. A signal cascade is usually initiated, altering the behavior of the cell (see cell signaling). Some CD proteins do not play a role in cell signalling, but have other functions, such as cell adhesion.

"Codon" means a three-nucleotide sequence potentially encoding a single amino acid.

"Consensus HA" means the hemagglutinin polypeptide encoded by the HAc polynucleotide.

"Cytokine" means any of a group of proteins and peptides that are used in organisms as signaling compounds. These chemical signals are similar to hormones and neurotransmitters and allow one cell to communicate with another.

"Epitope" means the part of a macromolecule that is recognized by the immune system, specifically by antibodies, B cells, or T cells. Although epitopes are usually thought to be derived from nonself proteins, sequences derived from the host that can be recognized are also classified as epitopes.

"ELISA" means Enzyme-Linked Immuno-Sorbent Assay; any enzyme immunoassay using an enzyme-labeled immunoreactant and an immunosorbent.

"ELIspot" means Enzyme-linked immunosorbent spot, a common method for monitoring immune responses in humans and animals. The ELISPOT assay is based on, and was developed from a modified version of the ELISA immunoassay. ELISPOT assays were originally developed to enumerate B cells secreting antigen-specific antibodies, and have subsequently been adapted for various tasks, especially the identification and enumeration of cytokine-producing cells at the single cell level. Simply put, at appropriate conditions the ELISPOT assay allows visualization of the secretory product of individual activated or responding cells. Each spot that develops in the assay represents a single reactive cell. Thus, the ELISPOT assay provides both qualitative (type of immune protein) and quantitative (number of responding cells) information.

"Glycosylated" means addition of saccharides to proteins and lipids. The process is one of four principal co-translational and post-translational modification steps in the synthesis of membrane and secreted proteins.

"Greater Affinity" means an increased bonding time or increased probability of bonding between a ligand and a receptor, or between two chemical entities.

"Growth Factor" means naturally occurring protein capable of stimulating cellular proliferation and cellular differentiation. Growth factors are important for regulating a variety of cellular processes. Growth factors typically act as signaling molecules between cells. Examples are cytokines and hormones that bind to specific receptors on the surface of their target cells.

They often promote cell differentiation and maturation, which varies between growth factors. For example, bone morphogenic proteins stimulate bone cell differentiation, while fibroblast growth factors and vascular endothelial growth factors stimulate blood vessel differentiation (angiogenesis).

"HAc" means a consensus polynucleotide of the H5N1 influenza family encoding a hemagglutinin polypeptide and having the following base pair sequence:

```
                                           (SEQ ID NO: 2)
ATG GAG AAG ATC GTG CTG CTG TTC GCC ATC GTG AGC

CTG GTG AAG AGC GAC CAG ATC TGC ATC GGA TCC CAC

GCC AAC AAC AGC ACC GAG CAG GTG GAC ACC ATC ATG

GAG AAG AAC GTG ACC GTG ACC CAC GCC CAG GAC ATC

CTG GAG AAG ACC CAC AAC GGC AAG CTG TGC GAC CTG

GAC GGC GTG AAG CCT CTG ATC CTG AGA GAC TGC AGC

GTG GCC GGC TGG CTG CTG GGC AAC CCT ATG TGC GAC

GAG TTC ATC AAC GTG CCT GAG TGG AGC TAC ATC GTG

GAG AAG GCC AAC CCT GCC AAC GAC CTG TGC TAC CCT

GGC GAC TTC AAC GAC TAC GAG GAG CTG AAG CAC CTG

CTG AGC AGA ATC AAC CAC TTC GAG AAG ATC CAG ATC

ATC CCT AAG AGC AGC TGG AGC AGC CAC GAG GCC AGC

AGC GGC GTG AGC AGC GCC TGC CCT TAC CAG GGC AAG

AGC AGC TTC TTC AGA AAC GTG GTG TGG CTG ATC AAG

AAG AAC AGC ACC TAC CCT ACC ATC AAG AGA AGC TAC

AAC AAC ACC AAC CAG GAG GAC CTG CTG GTG CTG TGG

GGC ATC CAC CAC CCT AAC GAC GCC GCC GAG CAG ACC

AAG CTG TAC CAG AAC CCT ACC ACC TAC ATC ACG GTG

GGC ACC AGC ACC CTG AAC CAG AGA CTG GTG CCT AAG

ATC GCC ACC AGA AGC AAG GTG AAC GGC CAG AGC GGC

AGA ATG GAG TTC TTC TGG ACC ATC CTG AAG CCT AAC

GAC GCC ATC AAC TTC GAG AGC AAC GGC AAC TTC ATC

GCC CCT GAG TAC GCC TAC AAG ATC GTG AAG AAG GGC

GAC AGC ACC ATC ATG AAG AGC GAG CTG GAG TAC GGC

AAC TGC AAC ACC AAG TGC CAG ACC CCT ATG GGC GCC

ATC AAC AGC AGC ATG CCT TTC CAC AAC ATC CAC CCT

CTG ACC ATC GGC GAG TGC CCT AAG TAC GTG AAG AGC

AAC AGA CTG GTG CTG GCC ACC GGC CTG AGA AAC AGC

CCT CAG AGA GAG AGA AGA AGA AAG AAG AGA GGC CTG

TTC GGC GCC ATC GCC GGC TTC ATC GAG GGC GGC TGG

CAG GGC ATG GTG GAC GGC TGG TAC GGC TAC CAC CAC

AGC AAC GAG CAG GGC AGC GGC TAC GCC GCC GAC AAG

GAG AGC ACC CAG AAG GCC ATC GAC GGC GTG ACC AAC

AAG GTG AAC AGC ATC ATC GAC AAG ATG AAC ACC CAG

TTC GAG GCC GTG GGC AGA GAG TTC AAC AAC CTG GAG

AGA AGA ATC GAG AAC CTG AAC AAG AAG ATG GAG GAC

GGC TTC CTG GAC GTG TGG ACC TAC AAC GCC GAG CTG

CTG GTG CTG ATG GAG AAC GAG AGA ACC CTG GAC TTC

CAC GAC AGC AAC GTG AAG AAC CTG TAC GAC AAG GTG

AGA CTG CAG CTG AGA GAC AAC GCC AAG GAG CTG GGC

AAC GGC TGC TTC GAG TTC TAC CAC AAG TGC GAC AAC

GAG TGC ATG GAG AGC GTG AGA AAC GGC ACC TAC GAC

TAC CCT CAG TAC AGC GAG GAG GCC AGA CTG AAG AGA

GAG GAG ATC AGC GGC GTG AAG CTG GAG AGC ATC GGC

ATC TAC CAG ATC CTG AGC ATC TAC AGC ACC GTG GCC

AGC AGC CTG GCC CTG GCC ATC ATG GTG GCC GGC CTG

AGC CTG TGG ATG TGC AGC AAC GGC AGC CTG CAG TGC

AGA ATC TGC ATC.
``` which HAc encodes the following polypeptide:

```
MEKIVLLFAIVSLVKSDQICIGSHANNSTEQV        (SEQ ID NO: 1)

DTIMEKNVTVTHAQDILEKTHNGKLCDLDGVK

PLILRDCSVAGWLLGNPMCDEFINVPEWSYIV

EKANPANDLCYPGDFNDYEELKHLLSRINHFE

KIQIIPKSSWSSHEASSGVSSACPYQGKSSFF

RNVVWLIKKNSTYPTIKRSYNNTNQEDLLVLW

GIHHPNDAAEQTKLYQNPTTYISVGTSTLNQR

LVPKIATRSKVNGQSGRMEFFWTILKPNDAIN

FESNGNFIAPEYAYKIVKKGDSTIMKSELEYG

NCNTKCQTPMGAINSSMPFHNIHPLTIGECPK

YVKSNRLVLATGLRNSPQRERRRKKRGLFGAI
```

```
AGFIEGGWQGMVDGWYGYHHSNEQGSGYAADK
ESTQKAIDGVTNKVNSIIDKMNTQFEAVGREF
NNLERRIENLNKKMEDGFLDVWTYNAELLVLM
ENERTLDFHDSNVKNLYDKVRLQLRDNAKELG
NGCFEFYHKCDNECMESVRNGTYDYPQYSEEA
RLKREEISGVKLESIGIYQILSIYSTVASSLA
LAIMVAGLSLWMCSNGSLQCRICI.
```

"Hemadsorption" means the adherence of red blood cells to other cells, particles or surfaces. Hemadsorption and hemadsorption inhibition are used for the assay of some viruses and their specific antibodies, e.g. paramyxovirus.

"Hemagglutinin" or "HA" means an antigenic glycoprotein found on the surface of the influenza viruses (as well as many other bacteria and viruses). It is responsible for binding the virus to the cell that is being infected. The name "hemagglutinin" comes from the protein's ability to cause red blood cells (erythrocytes) to clump together ("agglutinate") in vitro "Homologous" means having genetic sequences that share a high sequence identity or similarity.

"Humoral Immunity" means immune response mediated by B cells and involving circulating antibodies.

"Hybridize" means bonding or meshing with a complementary RNA or DNA (single strand or double strand) molecule.

"ID5" means a polynucleotide of the H5N1 influenza family encoding a hemagglutinin polypeptide and having the following base pair sequence:

```
(SEQ ID NO: 4)
ATG GAG AAG ATC GTG CTG CTG CTC GCC ATC GTG AGC
CTG GTG AAG AGC GAC CAG ATC TGC ATC GGA TCC CAC
GCC AAC AAC AGC ACC GAG CAG GTG GAC ACC ATC ATG
GAG AAG AAC GTG ACC GTG ACC CAC GCC CAG GAC ATC
CTG GAG AAG ACC CAC AAC GGC AAG CTG TGC GAC CTG
GAC GGC GTG AAG CCT CTG ATC CTG AGA GAC TGC AGC
GTG GCC GGC TGG CTG CTG GGC AAC CCT ATG TGC GAC
GAG TTC ATC AAC GTG CCT GAG TGG AGC TAC ATC GTG
GAG AAG GCC AAC CCT ACC AAC GAC CTG TGC TAC CCT
GGC TCC TTC AAC GAC TAC GAG GAG CTG AAG CAC CTG
CTG AGC AGA ATC AAC CAC TTC GAG AAG ATC CAG ATC
ATC CCT AAG AGC AGC TGG AGC GAC CAC GAG GCC AGC
AGC GGC GTG AGC AGC GCC TGC CCT TAC CTG GGC TCG
CCC AGC TTC TTC AGA AAC GTG GTG TGG CTG ATC AAG
AAG AAC AGC ACC TAC CCT ACC ATC AAG AAA AGC TAC
AAC AAC ACC AAC CAG GAG GAC CTG CTG GTG CTG TGG
GGC ATC CAC CAC CTC AAC GAC GCC GCC GAG CAG ACC
AAG CTG TAC CAG AAC CCT ACC ACC TAC ATC AGC ATC
GGC ACC AGC ACC CTG AAC CAG AGA CTG GTG CCT AAG
ATC GCC ACC AGA AGC AAG GTG AAC GGC CAG AGC GGC
AGA ATG GAC TTC TTC TGG ACC ATC CTG AAG CCT AAC
GAC GCC ATC AAC TTC GAG AGC AAC GGC AAC TTC ATC
GCC CCT GAG TAC GCC TAC AAG ATC GTG AAG AAA GGC
GAC AGC GCC ATC ATG AAG AGC GAG CTG GAG TAC GGC
AAC TGC AAC ACC AAG TGC CAG ACC CCT ATC GGC GCC
ATC AAC AGC AGC ATG CCT TTC CAC AAC ATC CAC CCT
CTG ACC ATC GGC GAG TGC CCT AAG TAC GTG AAG AGC
AAC AGA CTG GTG CTG GCC ACC GGC CTG AGA AAC AGC
CCT CAG AGA GAG TCA AGA AGA AAG AGA GGC CTG TTC
GGC GCC ATC GCC GGC TTC ATC GAG GGC GGC TGG CAG
GGC ATG GTG GAC GGC TGG TAC GGC TAC CAC CAC AGC
AAC GAG CAG GGC AGC GGC TAC GCC GCC GAC AAG GAG
AGC ACC CAG AAG GCC ATC GAC GGC GTG ACC AAC AAG
GTG AAC AGC ATC ATC GAC AAG ATG AAC ACC CAG TTC
GAG GCC GTG GGC AGA GAG TTC AAC AAC CTG GAG AGA
AGA ATC GAG AAC CTG AAC AAG AAG ATG GAG GAC GGC
TTC CTG GAC GTG TGG ACC TAC AAC GCC GAG CTG CTG
GTG CTG ATG GAG AAC GAG AGA ACC CTG GAC TTC CAC
GAC AGC AAC GTG AAG AAC CTG TAC GAC AAG GTG AGA
CTG CAG CTG AGA GAC AAC GCC AAG GAG CTG GGC AAC
GGC TGC TTC GAG TTC TAC CAC AAG TGC GAC AAC GAG
TGC ATG GAG AGC ATC AGA AAC GGC ACC TAC AAC TAC
CCT CAG TAC AGC GAG GAG GCC AGA CTG AAG AGA GAG
GAG ATC AGC GGC GTG AAG CTG GAG AGC ATC GGC ACC
TAC CAG ATC CTG AGC ATC TAC AGC ACC GTG GCC AGC
AGC CTG GCC CTG GCC ATC ATG ATG GCC GGC CTG AGC
CTG TGG ATG TGC AGC AAC GGC AGC CTG CAG TGC AGA
ATC TGC ATC.
```

Which polynucleotide sequence encodes an amino acid having the following amino acid sequence:

```
MEKIVLLLAIVSLVKSDQICIGSHANNSTEQV          (SEQ ID NO: 3)
DTIMEKNVTVTHAQDILEKTHNGKLCDLDGVK
PLILRDCSVAGWLLGNPMCDEFINVPEWSYIV
EKANPTNDLCYPGSFNDYEELKHLLSRINHFE
KIQIIPKSSWSDHEASSGVSSACPYLGSPSFF
RNVVWLIKKNNTYPTIKKSYNNTNQEDLLVLW
GIHHPNDAAEQTRLYQNPTTYISIGTSTLNQR
LVPKIATRSKVNGQSGRMEFFWTILKPNDAIN
FESNGNFIAPEYAYKIVKKGDSAIMKSELEYG
```

```
-continued
NCNTKCQTPMGAINSSMPFHNIHPLTIGECPK

YVKSNQLVLATGLRNSPQRESRRKKRGLFGAI

AGFIEGGWQGMVDGWYGYHHSNEQGSGYAADK

ESTQKAIDGVTNKVNSIIDKMNTQFEAVGREF

NNLERRIENLNKKMEDGFLDVWTYNAELLVLM

ENERTLDFHDSNVKNLYDKVRLQLRDNAKELG

NGCFEFYHKCDNECMESIRNGTYNYPQYSEEA

RLKREEISGVKLESIGTYQILSIYSTVASSLA

LAIMMAGLSLWMCSNGSLQCRICI.
```

"$LD_{50}$" means the point at which a given dose is lethal to 50% of a test population.

"Maintenance Of Basal Body Weight In Subjects" means maintenance of body weight as compared to body weight pre-treatment.

"Maintenance Of Basal Body Temperature" means maintenance of body temperature as compared to body temperature pre-treatment.

"Oligonucleotide" means a short sequence of nucleotides (RNA or DNA), typically with twenty or fewer bases "pAnhui" means the Anhui polynucleotide encompassed in a plasmid vector.

"pHAc" means the HAc consensus HA polynucleotide encompassed in a plasmid vector.

"pID5" means the ID5 polynucleotide encompassed in a plasmid vector.

"Polynucleotide" means an organic polymer molecule composed of nucleotide monomers covalently bonded in a chain. DNA (deoxyribonucleic acid) and RNA (ribonucleic acid) are examples of polynucleotides with distinct biological functions. Polynucleotides can also be made artificially from oligonucleotides, smaller nucleotide chains with generally fewer than 30 subunits.

"Polypeptide" means an amino acid sequence derived from the specified protein or proteins and further to homologous peptides derived from equivalent regions of proteins homologous to the specified proteins of the same or other species. The term further relates to permissible amino acid alterations and peptidomimetics designed based on the amino acid sequence of the specified proteins or their homologous proteins.

"Resistance" means ability of a subject to avoid the decreased weight, and decreased body temperature, and increased mortality associated with influenza infection or influenza-like antigen presentation. "Resistance" also means the ability to mount a vigorous cellular and/or humoral immune response to any such infection, as can be assayed, for example, by measurement of antibody titer or release of interferon-γ from CD8-positive immune system cells.

"Reassortant Virus" means a virion containing nucleic acid and/or protein coat from more than one virus species.

"Titer" means a measurement of proteins that are found in blood or other bodily fluids of vertebrates, and are used by the immune system to identify and neutralize foreign objects, such as bacteria and viruses. Such proteins are often specific to a particular antigen, for example, hemagglutinin antigens of the influenza viral family.

"Vector" means any type of delivery system known in the art capable of delivering or assisting to deliver a DNA or RNA fragment to the interior of a eukaryotic cell (e.g., without limitation, plasmids, cosmids, phage, viruses, virus fragments, etc.)

"Viral Challenge" means infection by at least one viral particle, in whole or in part, in vivo or in vitro. "Viral Challenge" may also be defined as contacting a subject with a viral particle or particle fragment that is no longer viable; and encompasses contact of a subject with a pseudovirus or other molecular construct presenting virus-specific antigens.

"Virosome" means a vector containing a membrane-bound hemagglutinin and neuraminidase derived from the influenza virus, which serves to amplify fusogenic activity and therefore facilitate the uptake of material within the virosome into antigen presenting cells (APC) and induce a natural antigen-processing pathway.

"Wild type" means the typical form of an organism, strain, gene, or characteristic as it occurs in nature.

In some embodiments, this disclosure provides an isolated polynucleotide comprising a nucleic acid sequence corresponding to or homologous to SEQ ID NO. 2.

In some embodiments, this disclosure provides an isolated polynucleotide comprising a nucleic acid sequence corresponding to or homologous to SEQ ID NO. 4.

In some embodiments, this disclosure provides an isolated polynucleotide comprising a nucleic acid sequence corresponding to or homologous to SEQ ID NO. 6.

In some embodiments, this disclosure provides an isolated polynucleotide comprising a nucleic acid sequence corresponding to or homologous to at least one of SEQ ID NOS: 2, 4, or 6.

In some embodiments, this composition comprises at least two of the polynucleotides homologous to SEQ ID NOS. 2, 4, or 6.

In some embodiments, this disclosure provides a composition comprising the isolated polynucleotide of at least one of SEQ. ID NOs. 2, 4, or 6 above.

In some embodiments, the composition further includes a vector.

In some embodiments, the composition is a vector.

In some embodiments, the vector is a liposome, virosome or cell.

In some embodiments, the vector is a plasmid.

In some embodiments, the composition further comprises a polysaccharide encoding a growth factor or cytokine.

In some embodiments, the composition additionally comprises a growth factor, an adjuvant, an excipient, or a combination thereof.

In some embodiments, this disclosure provides an oligonucleotide specifically hybridizing with a polynucleotide of the disclosure.

In some embodiment, the oligonucleotide specifically hybridizing with the polynucleotide of the disclosure exhibits greater affinity for the polynucleotide, as compared to a polynucleotide comprising a wild type influenza sequence.

In some embodiments, this disclosure provides a method of treating, reducing the incidence of, reducing the severity of, delaying onset of, or ameliorating symptoms associated with influenza infection in a subject, the method comprising contacting a cell in a subject prior to infection, infected with, and/or at risk of infection with an influenza virus with a sufficient amount of isolated polynucleotide comprising an nucleic acid sequence corresponding to, or homologous to that set forth in at least one of SEQ ID NOS: 2, 4, or 6 or any combination thereof so as to increase a subject's resistance to influenza virus upon viral challenge.

In some embodiments, the cell in a subject is contacted with a composition or vector that is the polynucleotide.

In some embodiments, the cell in a subject is contacted with a composition or vector that contains the polynucleotide.

In some embodiments, the subject's resistance is increased relative to a particular clade of influenza virus.

In some embodiments, the subject's resistance is increased relative to numerous clades of influenza virus.

In some embodiments, the subject's resistance is increased relative to reassortant influenza virus.

In some embodiments, the administration of an isolated polynucleotide enables the subject to produce a polypeptide coded for by the isolated polynucleotide.

In some embodiments, the polypeptide coded for by the isolated polynucleotide is capable of glycosylation.

In some embodiments, the polypeptide coded for by the isolated polynucleotide is subsequently processed by the subject and at least some portion of the polypeptide coded for by the isolated polynucleotide is presented as an epitope by an antigen-presenting cell of the subject.

In some embodiments, the increased resistance is quantifiable as an increase in antibody titer following initial administration of the polypeptide or combination of polypeptides.

In some embodiments, the increased resistance to viral challenge is quantifiable as an increase in interferon-γ produced by CD-8 positive immune cells characterizable as a component of a cellular immune system.

In some embodiments, the increased resistance to viral challenge is quantifiable as decreased mortality in subjects.

In some embodiments, the increased resistance to viral challenge is quantifiable as decreased hemadsorption in subject cells.

In some embodiments, the increased resistance to viral challenge is quantifiable as maintenance of basal body weight in subjects.

In some embodiments, codon usage of the isolated polynucleotide of the present disclosure has been optimized for mammalian expression of an influenza hemagglutinin (HA) polypeptide sequence or a derivative thereof.

In some embodiments, this disclosure provides a composition comprising an isolated polypeptide comprising an amino acid sequence corresponding to, or homologous to that of SEQ ID NO. 1.

In some embodiments, this disclosure provides a composition comprising an isolated polypeptide comprising an amino acid sequence corresponding to, or homologous to that of SEQ ID NO. 3.

In some embodiments, this disclosure provides a composition comprising an isolated polypeptide comprising an amino acid sequence corresponding to, or homologous to that of SEQ ID NO. 5.

In some embodiments, this disclosure provides a composition comprising the polypeptide.

In some embodiments, the polypeptide is capable of glycosylation.

In some embodiments, the polypeptide is glycosylated.

In some embodiments, the polypeptide is processed by an antigen-processing cell of the subject wherein some component of the polypeptide is subsequently presented as an epitope by the antigen-presenting cell.

In some embodiments, this disclosure provides a composition comprising at least two of the polypeptides homologous to SEQ ID NOs. 1, 3, or 5.

In some embodiments, the composition further comprises a vector.

In some embodiments, the vector is a liposome, virosome or cell.

In some embodiments, the composition additionally comprises a vector comprised of the polynucleotides and liposomes, cells and/or compositions comprising the same.

In some embodiments, the composition additionally comprises a growth factor, an adjuvant or a combination thereof.

In some embodiments, the composition further comprises a cytokine, a growth factor, an antiviral, an adjuvant, or a combination thereof.

In some embodiments, this disclosure provides an antibody specifically binding to a polypeptide and/or glycosylated polypeptide of this disclosure.

In some embodiments, this disclosure provides a method of treating, reducing the incidence of, reducing the severity of, delaying onset of, or ameliorating symptoms associated with influenza infection in a subject, the method comprising contacting a cell in a subject prior to infection, at risk of infection and/or infected with an influenza virus with a sufficient amount of isolated polypeptide comprising an amino acid sequence corresponding to, or homologous to that set forth in SEQ ID NOS: 1, 3, or 5 so as to increase a subject's resistance to influenza virus upon viral challenge.

In some embodiments, the subject cell is contacted with the isolated polypeptide.

In some embodiments, the subject cell is contacted with a composition containing the isolated polypeptide.

In some embodiments, the isolated polypeptide is glycosylated prior to administration.

In some embodiments, the isolated polypeptide is glycosylated subsequent to administration.

In some embodiments, the increased resistance to viral challenge is quantifiable as an increase in antibody titer following initial administration of the polypeptide or combination of polypeptides.

In some embodiments, the increased resistance to viral challenge is quantifiable as an increase in interferon-γ produced by CD-8 positive cell-based immune cells.

In some embodiments, the increased resistance to viral challenge is quantifiable as decreased mortality in subjects.

In some embodiments, the increased resistance to viral challenge is quantifiable as decreased hemadsorption in subject cells.

In some embodiments, the increased resistance to viral challenge is quantifiable as maintenance of basal body weight in subjects.

In some embodiments, the methods of this disclosure further comprise repeat administration of the isolated polypeptide or polypeptides to the subject.

In some embodiments, viral challenge encompasses challenge with an influenza virus.

In some embodiments, viral challenge encompasses challenge with an influenza virus of a single clade.

In some embodiments, viral challenge encompasses challenge with a reassortant virus.

In some embodiments, viral challenge is accomplished deliberately, that is through conscious introduction or administration of the virus to a subject.

In some embodiments, viral challenge occurs as a function of natural etiologic processes associated with viral infectivity and propagation.

In some embodiments, the influenza virus is a H5 strain.

In some embodiments, the influenza virus is a H5N1 strain.

In some embodiments, the viral challenge consists of multiple types of influenza virus.

In some embodiments, the viral challenge consists of one or more clades of virus that are the product of viral resortment.

In some embodiments, the subject is capable of resisting subsequent viral challenge by an influenza virus of an alternate clade or subclade than that characterized by the administered polynucleotide or polysaccharide.

In some embodiments, the subject is capable of resisting multiple viral challenges.

In some embodiments, the subject is capable of resisting multiple viral challenges of alternate clades.

This disclosure provides, in some embodiments, an HA-based DNA vaccine against H5N1 viruses, which has been optimized for expression in mammals, which is capable of conferring protection from a mucosal challenge of a lethal dose of NIBRG-14, a reassortant influenza virus with H5N1 Vietnam 1194 HA, in mouse models, as exemplified herein. In other embodiments, this disclosure provides HA-based DNA vaccines against H5N1 clade 2.1 and 2.3, which have been optimized for expression in mammals, which are capable of conferring protection from mucosal challenges of a lethal dose of RG2 (reassortant of H5N1 virus strain Indonesia/5/2005) and RG5 (reassortant of H5N1 viral strain (Anhui/01/2005 (H5N1)/PR8-IBCDC-RG5).

In one embodiment, this disclosure provides an isolated polypeptide comprising an amino acid sequence corresponding to, or homologous to that set forth in any of SEQ ID NOs: 1, 3, and/or 5. In one embodiment, this disclosure provides a composition comprising the polypeptide, and in some embodiments, further comprises a cytokine, a growth factor, an antiviral, an adjuvant, or a combination thereof.

In yet other embodiments, the disclosure comprises isolated or recombinant polypeptides, that comprise an amino acid sequence that shares at least 75%, or in some embodiments, at least 85%, or at least 90% or at least 95% identity over at least about 350 amino acids; over at least about 400 amino acids; over at least about 450 amino acids; over at least about 500 amino acids; over at least about 525 amino acids; over at least about 550 amino acids; over at least about 555 amino acids; over at least about 560 amino acids; or over at least about 565 amino acids contiguous of any of the described polypeptides. In some embodiments, the polypeptide sequence (e.g., as listed in the sequence listing herein) comprises less than 569, 555, etc. amino acids.

In some embodiments, the polypeptides of the disclosure optionally comprise fusion proteins, proteins with a leader sequence, a precursor polypeptide, proteins with a secretion signal or a localization signal, or proteins with an epitope tag, an E-tag, or a His epitope tag.

In some embodiments, the disclosure comprises a polypeptide comprising a sequence having at least 75%, at least 80%, at least 85%, at least 90%, at least 93%, at least 95%, at least 98%, at least 98.5%, at least 99%, at least 99.2%, at least 99.4%, at least 99.6%, at least 99.8%, or at least 99.9% sequence identity to a sequence as set forth in SEQ ID NOs: 1, 3, and/or 5.

It is to be understood that this disclosure is directed to a polypeptide as described herein, or a fragment thereof/a functional fragments thereof, or any manipulation thereof, including, for example, truncations, substitutions, insertions, epitopes, any modification as will be known to one skilled in the art, producing an immunogenic HA polypeptide, which confers protection across different clades and/or subclades.

The hemagglutinin sequences of the disclosure may comprise the endogenous amino terminal signal peptide sequences, however, the hemagglutinin polypeptide sequences of the disclosure also include the mature (amino terminal signal peptide cleaved) form of the hemagglutinin polypeptides. The cleavage sites of any hemagglutinin polypeptide sequence of any influenza strain can be routinely measured or predicted using any number of methods in the art.

In other aspects, the disclosure comprises a composition with one or more polypeptides as described herein, or fragments thereof. The disclosure also includes polypeptides that are specifically bound by a polyclonal antisera raised against at least 1 antigen that comprises at least one amino acid sequence described herein, or a fragment thereof. Such antibodies specific for the polypeptides described above are also features of the disclosure. The polypeptides of the disclosure are optionally immunogenic.

The disclosure also encompasses immunogenic compositions comprising an immunologically effective amount of one or more of any of the polypeptides described above as well as methods for stimulating the immune system of an individual to produce a protective immune response against influenza virus by administering to the individual an immunologically effective amount of any of the above polypeptides in a physiologically acceptable carrier.

Additionally, the disclosure includes recombinant virus, and in some embodiments, recombinant influenza virus that comprises one or more of the polypeptides or polynucleotides above, in addition to immunogenic compositions comprising an immunologically effective amount of such recombinant influenza virus.

In some embodiments, the polypeptides, polynucleotides, and constructs/vectors of this disclosure comprise influenza sequences, which are not native sequences. In some embodiments, the polypeptides, polynucleotides, and constructs/vectors of this disclosure comprise sequences derived from a given influenza strain, which is optimized to produce an immune response, which is cross-reactive with multiple viral subclades and/or viral clades.

Methods for stimulating the immune system of an individual to produce a protective immune response against influenza virus, through administering an immunologically effective amount of such recombinant influenza virus in a physiologically acceptable carrier are also part of the disclosure.

In one embodiment, this disclosure provides an antibody specifically binding to a polypeptide of this disclosure.

In one embodiment, this disclosure provides an isolated polynucleotide comprising a nucleic acid sequence corresponding to or homologous to at least one of SEQ ID NOs: 2, 4, or 6.

In one embodiment, this disclosure provides an oligonucleotide specifically hybridizing with a polynucleotide of the disclosure, which in some embodiments, exhibits greater affinity for the polynucleotide, as compared to a polynucleotide comprising a wild type influenza sequence.

In some embodiments, this disclosure provides a vector comprising the polynucleotides of this disclosure and liposomes, cells and/or compositions comprising the same.

In some embodiments, the disclosure comprises an isolated or recombinant nucleic acid having a sequence sharing at least 75%, or at least 80%, or at least 85%, or at least 90%, or at least 95%, or corresponding to that set forth in any of SEQ ID NOs:2, 4, and/or 6 (or complementary sequences thereof), a polynucleotide sequence which hybridizes under highly stringent conditions over substantially the entire length of any of the above polynucleotide sequences, and a polynucleotide sequence comprising all or a fragment of any of such polynucleotide sequences wherein the sequence preferably encodes a hemagglutinin polypeptide or a fragment of a hemagglutinin polypeptide, which, when contacted with a cell in a subject produces an immune response either directly (e.g. polynucleotide as antigen) or indirectly (e.g., polynucleotide is incorporated by the cell and is subsequently translated and transcribed to yield an immunogenically active polypeptide or epitope), which is cross-reactive with multiple influenza clades and subclades.

It is to be understood that this disclosure is directed to a polynucleotide as described herein, or a fragment thereof a functional fragments thereof, or any manipulation thereof, including, for example, truncations, substitutions, insertions, any modification as will be known to one skilled in the art, encoding an immunogenic HA polypeptide, which confers protection across different clades and/or subclades.

Protocols for introducing the nucleic acids, vectors, etc. of the disclosure into cells may comprise, for example: direct DNA uptake techniques, virus, plasmid, linear DNA or liposome mediated transduction, or transfection, magnetoporation methods employing calcium-phosphate mediated and DEAE-dextran mediated methods of introduction, electroporation, direct injection, and receptor-mediated uptake (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). It is to be understood that any direct means or indirect means of intracellular access of a virus, nucleic acid or vector of the disclosure is contemplated herein, and represents an embodiment thereof.

The disclosure also includes an isolated or recombinant nucleic acid that encodes an amino acid sequence which is substantially identical over at least about 300 amino acids of any of the above nucleic acids, or over at least about 350 amino acids; over at least about 400 amino acids; over at least about 450 amino acids; over at least about 500 amino acids; over at least about 502 amino acids; over at least about 550 amino acids; over at least about 559 amino acids; over at least about 565 amino acids; or over at least about 566 amino acids of any of the above nucleic acids. Again, in situations wherein the amino acid is less than, e.g., 566, 565, 559, etc. in length (e.g., see, Sequence Listing) then it should be understood that the length is optionally less than 566, 565, 559, etc. The disclosure also includes any of the above nucleic acids that comprise a hemagglutinin polypeptide, or one or more fragments of one or more hemagglutinin polypeptides. Other aspects of the disclosure include isolated or recombinant nucleic acids that encode a polypeptide whose sequence has at least 98% identity, at least 98.5% identity, at least 99% identity, at least 99.2% identity, at least 99.4% identity, at least 99.6% identity, at least 99.8% identity, or at least 99.9% identity to at least one of the above described polynucleotides. The disclosure also includes isolated or recombinant nucleic acids encoding a polypeptide of hemagglutinin produced by mutating or recombining one or more above described polynucleotide sequences. The polynucleotide sequences of the disclosure can optionally comprise one or more of, e.g., a leader sequence, a precursor sequence, or an epitope tag sequence or the like, and can optionally encode a fusion protein (e.g., with one or more additional nucleic acid sequences).

As used herein, the term "correspond to" or "correspondance" in reference to a protein or nucleic acid refers to an amino acid or nucleic acid sequence, respectively, that is identical to the reference sequence. The terms "homology", "homologue" or "homologous", in any instance, indicate that the nucleic acid or amino acid sequence referred to, exhibits, in one embodiment at least 70% correspondence with the indicated sequence.

In another embodiment, the nucleic acid or amino acid sequence exhibits at least 75% correspondence with the indicated sequence. In another embodiment, the nucleic acid or amino acid sequence exhibits at least 80% correspondence with the indicated sequence. In another embodiment, the nucleic acid or amino acid sequence exhibits at least 85% correspondence with the indicated sequence. In another embodiment, the nucleic acid or amino acid sequence exhibits at least 90% correspondence with the indicated sequence. In another embodiment, the nucleic acid or amino acid sequence exhibits at least 95% or more correspondence with the indicated sequence. In another embodiment, the nucleic acid or amino acid sequence exhibits 95-100% correspondence with the indicated sequence.

In other embodiments, the disclosure comprises a composition comprising two or more above described polypeptides or nucleic acids. In some embodiments, the composition may comprise a library comprising at least about 2, 5, 10, 50 or more nucleic acids. Such compositions can optionally be produced by cleaving one or more above described nucleic acid (e.g., mechanically, chemically, enzymatically with a restriction endonuclease/RNAse/DNAse, etc.). Other compositions of the disclosure include, e.g., compositions produced by incubating one or more above described nucleic acid in the presence of deoxyribonucleotide triphosphates and a thermostable nucleic acid polymerase.

The disclosure also encompasses cells comprising at least one of the above described nucleic acids, or a cleaved or amplified fragment or product thereof. Such cells can optionally express a polypeptide encoded by such nucleic acid. Other embodiments of the disclosure include vectors (e.g., plasmids, cosmids, phage, viruses, virus fragments, etc.) comprising any of above described nucleic acids. Such vectors can optionally comprise an expression vector. Cells transduced by such vectors are also within the current disclosure.

In some embodiments, the disclosure encompasses a virus (e.g., an influenza virus) comprising one or more above described nucleic acids (e.g., encoding hemagglutinin and optionally a neuraminidase), or one or more fragments thereof. Immunogenic compositions comprising such virus are also part of the current disclosure. Such viruses can comprises a reassortant virus such as a 6:2 reassortant virus (e.g., comprising 6 gene encoding regions from one or more donor virus and 2 gene encoding regions from one or more above described nucleotide sequence (or one or more fragment thereof) which can optionally comprise hemagglutinin and/or neuraminidase). Reassortant viruses (optionally live viruses) of the disclosure can include donor viruses that are one or more of, e.g., cold-sensitive, cold-adapted, or an attenuated. For example, reassortant viruses can comprise e.g., A/Ann Arbor/6/60, PR8, etc. Reassortant viruses of the disclosure may alternatively exclude A/Ann Arbor/6/60. One preferred embodiment of the disclosure is a reassortant influenza virus, wherein the virus is a 6:2 reassortant influenza virus and comprises 6 gene encoding regions from A/Ann Arbor/6/60 and 2 gene encoding regions that encode a polypeptide. In an alternative embodiment, a reassortant influenza virus of the disclosure includes a 6:2 reassortant influenza virus, wherein said virus comprises 6 gene encoding regions from one or more donor viruses other than A/Ann Arbor/6/60 and 2 gene encoding regions that encode a polypeptide. In another alternative embodiment, a reassortant influenza virus of the disclosure includes a 6:2 reassortant influenza virus, wherein said virus comprises 6 gene encoding regions from one or more donor viruses other than A/Ann Arbor/6/60 and 2 gene encoding regions, wherein the 2 gene encoding regions are HA or NA polypeptides from any pandemic influenza strain. Methods of producing recombinant influenza virus through culturing a host cell harboring an influenza virus in a suitable culture medium under conditions permitting expression of nucleic acid and, isolating the recombinant influenza virus from one or more of the host cell or the medium are also part of the disclosure.

In some embodiments, the disclosure encompasses a subunit vaccine, which comprises influenza HA derived polypeptides. In some embodiments, such polypeptides are consensus sequences derived by computer modeling, as known in the art, and may comprise sequences optimized for mammalian expression. In some embodiments, such vaccines comprise consensus sequences derived from known Clades, reassortant viruses, and predicted mutants, as will be appreciated by one skilled in the art.

In other embodiments herein, the disclosure comprises immunogenic compositions having an immunologically effective amount of any of the above described polypeptides, polynucleotides, constructs and/or cells described herein. Other embodiments include methods for stimulating the immune system of an individual to produce a protective immune response against influenza virus by administering to the individual an immunologically effective amount of any of the above described polypeptides, polynucleotides, constructs and/or cells described (optionally in a physiologically effective carrier).

Other aspects of the disclosure include methods of producing an isolated or recombinant polypeptide by culturing any host cell above, in a suitable culture medium under conditions permitting expression of nucleic acid and, isolating the polypeptide from one or more of the host cells or the medium in which is the cells are grown.

According to another embodiment, nucleic acid vectors comprising the isolated nucleic acid sequences delineated herein include a promoter for regulating expression of the isolated nucleic acid. Such promoters are known to be cis-acting sequence elements required for transcription as they serve to bind DNA dependent RNA polymerase, which transcribes sequences present downstream thereof.

A vector according to the present disclosure preferably further includes an appropriate selectable marker. The vector may further include an origin of replication, and may be a shuttle vector, which can propagate both in bacteria, such as, for example, *E. coli* (wherein the vector comprises an appropriate selectable marker and origin of replication) and be compatible for propagation in vertebrate cells, or integration in the genome of an organism of choice. The vector according to this aspect of the present disclosure can be, for example, a plasmid, a bacmid, a phagemid, a cosmid, a phage, a virus or an artificial chromosome.

In another aspect of the present disclosure there is provided a host cell containing the nucleic acid vectors as described herein. The cell may be a prokaryotic or a eukaryotic cell.

The nucleic acids of the present disclosure may be comprised of a nucleic acid sequence that is at least 70%, at least 75%, at least 80%, at least 85%, at least 90%, at least 95% or more, including 95%-100% homology or identity to SEQ ID NO: 2, as determined by, for example, the Smith-Waterman algorithm, utilized in analyzing sequence alignment protocols, as in for example, the GAP, BESTFIT, FASTA and TFASTA programs in the Wisconsin Genetics Software Package release 7.0, Genetics Computer Group, 575 Science Dr., Madison, Wis.).

Alternatively or additionally, polynucleotide homology may be determined by hybridization to SEQ ID No: 2, which may be effected by stringent or moderate hybridization conditions. An example of stringent hybridization is the use of a hybridization solution containing 10% dextran sulfate, 1 M NaCl, 1% SDS and 5×10⁶ cpm $^{32}$P labeled probe, at 65° C., with a final wash solution of 0.2×SSC and 0.1% SDS and final wash at 65° C.; whereas an example of moderate hybridization would be the use of a hybridization solution containing 10% dextran sulfate, 1 M NaCl, 1% SDS and 5×10⁶ cpm $^{32}$P labeled probe, at 65° C., with a final wash solution of 1×SSC and 0.1% SDS and final wash at 50° C.

Immunogenic compositions are also features of the disclosure. For example, immunogenic compositions comprising one or more of any of the polypeptides and/or nucleic acids described above and, optionally, an excipient such as a pharmaceutically acceptable excipient or one or more pharmaceutically acceptable administration component. Immunogenic compositions of the disclosure can also comprise any one or more above described virus as well (e.g., along with one or more pharmaceutically acceptable administration component).

In some embodiments, any of the compositions for use in this disclosure will comprise a polypeptide, polynucleotide, vector, cell or liposome, in any form or embodiment as described herein. In some embodiments, any of the compositions for use in this disclosure will consist of a polypeptide, polynucleotide, vector, cell or liposome in any form or embodiment as described herein. In some embodiments, the compositions for use in this disclosure will consist essentially of a polypeptide, polynucleotide, vector, cell or liposome in any form or embodiment as described herein. In some embodiments, the term "comprise" refers to the inclusion of the indicated active agent, as well as inclusion of other active agents, and pharmaceutically acceptable carriers, excipients, emollients, stabilizers, etc., as are known in the pharmaceutical industry. In some embodiments, the term "consisting essentially of refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting essentially of may refer to components, which may still be active for the described indication, however, they differ in terms of structure, class, activity, mode of action, etc., from that of the reference compound. In some embodiments, the term "consisting" refers to a composition, which contains the active ingredient and a pharmaceutically acceptable carrier or excipient.

Methods of producing immunogenic responses in a subject through administration of an effective amount of any of the above polypeptides, polynucleotides, vectors, cells, compositions or liposomes to a subject are also within the current disclosure. Additionally, methods of prophylactic or therapeutic treatment of a viral infection (e.g., viral influenza) in a subject through administration of any one or more above described polypeptides, polynucleotides, vectors, cells, compositions or liposomes in an amount effective to produce an immunogenic response against the viral infection are also part of the current disclosure. Subjects for such treatment can include mammals (e.g., humans). Such methods can also comprise in vivo administration to the subject as well as in vitro or ex vivo administration to one or more cells of the subject. Additionally, such methods can also comprise administration of a composition of the virus and a pharmaceutically acceptable excipient that are administered to the subject in an amount effect to prophylactically or therapeutically treat the viral infection.

In some embodiments of the disclosure the compositions comprise consensus HA sequences derived of one or more pandemic influenza strains. In some embodiments of the disclosure the compositions comprise consensus HA sequences derived of one or more pandemic influenza strain and sequences encoding a selected backbone strain in a 6:2 reassortant. The disclosure also includes live attenuated vaccines comprising such above compositions, including bacterial or viral vectors encoding the sequences herein described.

In some embodiments, with respect to the indicated HA sequences representing derivatives of the indicated strain, the term "derivative" and "variant" with respect to an indicated nucleic acid or polypeptide refers to a sequence that is altered by one or more nucleotides, or amino acids, respectively, with respect to a reference sequence.

The derivative or variant can have "conservative" changes, wherein a substituted nucleotide, or amino acid, respectively has similar structural or chemical properties, e.g., replacement of leucine with isoleucine, or nucleotides encoding the same. Alternatively, a variant can have "nonconservative" changes, e.g., replacement of a glycine with a tryptophan, or nucleotides encoding the same. Analogous minor variation can also include amino acid/nucleic acid deletion or insertion, or both. Guidance in determining which residues can be substituted, inserted, or deleted without eliminating biological or immunological activity can be found using computer programs well known in the art, for example, DNASTAR software.

In some embodiments, the polynucleotides, polypeptides, vectors, cells, compositions, etc., of this disclosure comprise a consensus HA derived from an influenza H5N1 virus, or a variant thereof. The H5N1 viruses may be comprised of any clade or subclade thereof, including clade 1, 2 or 3 viruses and sub-clades thereof. For example, the viruses may include at least any of the following recognized influenza viral types: ck/Cambodia/013LC1b/05, Vietnam/1194/04*, Vietnam/1203/04*, Vietnam/HN30408/05, Thailand/16/04, Vietnam/JPHN30321/05, Hong Kong/213/03, Indonesia/CDC523/06, Indonesia/CDC699/06, Indonesia/CDC326/06, Indonesia/5/05*, Indonesia/CDC184/05, Indonesia/7/05, dk/Kulon-ProgoBBVET9/04, ck/Indonesia/CDC25/05, Indonesia/6/05, ck/Brebes/BBVET2/05, Indonesia/CDC594/06#, ck/Dairi/BPPV1/05, ck/Yunnan/374/04, ck/Yunnan/115/04, ck/Yunnan/493/05, ck/Yunnan/447/05, dk/Guangxi/13/04, ck/Guangxi/12/04, whooping swan/Mongolia/244/05*, bar headed gs/Qinghai/IA/05*, Turkey/65596/06, Turkey/15/06, fraq/207NAMRU3/06, ck/Nigeria/641/06, mid/Italy/332/06, turkey/Turkey/1/05*, E t/2782NAMRU3/06, Djibouti/5691NAMRU3/06, ck/Nigeria42/06, migratory dk/Jiangxi/2136/05, gs/Kazakhstan/464/05, ck/Krasnodar/01/06, Azerbaijan/011162/06, Indonesia/CDC625/06 #, Hong Kong/156/97, swan/Iran/754/06, dk/Laos3295/06, Anhui/1/05*, Anhui/2/05, Japanese white-eye/Hong Kong/1038/06, ck/Malaysia935/06, Vietnam/30850/05, Guangxi/1/05, dk/Hunan/15/04, qa/Guangxi/575/05, dk/Vietnam/Ncvdcdc95/05, migratory dk/Jiangxi/1653/05, gs/Guangdong/1/96, or in some embodiments, a consensus sequence is derived of combinations thereof. In some embodiments, this disclosure is directed to vaccination of a subject with such a consensus polynucleotide or polypeptide, and protection or a therapeutic or prophylactic advantage is afforded to the subject, upon exposure to multiple clades or subclades, such that the consensus sequence derived is cross-protective across different clades and/or subclades.

In some embodiments, the consensus amino acid sequence will comprise any of the amino acid sequences set forth in SEQ ID NOS. 1, 3, and/or 5

In some embodiments, the consensus sequence is encoded by a polynucleotide as set forth in SEQ ID NOs: 2, 4 and/or 6.

In some embodiments, this disclosure provides a method of treating, reducing the incidence of, reducing the severity of, delaying onset of, or ameliorating symptoms associated with influenza infection in a subject, the method comprising contacting a cell in a subject infected with, or at risk of infection with an influenza virus with an isolated polypeptide comprising an amino acid sequence corresponding to, or homologous to that set forth in SEQ ID NOs: 1, 3, and/or 5.

In some embodiments, this disclosure provides a method of treating, reducing the incidence of, reducing the severity of, delaying onset of, or ameliorating symptoms associated with influenza infection in a subject, said method comprising administering a sufficient amount of an isolated polynucleotide homologous to or corresponding to SEQ ID NOs 2, 4, and/or 6 so as to confer subsequent resistance to viral challenge.

In some embodiments, this disclosure provides a method of treating, reducing the incidence of, reducing the severity of, delaying onset of, or ameliorating symptoms associated with influenza infection in a subject, said method comprising contacting a cell in a subject infected with, or at risk of infection with an influenza virus with an isolated polynucleotide, wherein said polynucleotide comprises a nucleic acid sequence, in which codon usage has been optimized for mammalian expression of an influenza hemagglutinin (HA) or a derivative thereof.

As used herein, the term "treating" includes preventative as well as disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

In one embodiment, "treating" refers to both therapeutic treatment and prophylactic or preventative measures, wherein the object is to prevent or lessen infection as described herein above. Thus, in one embodiment, treating may include directly affecting or curing, suppressing, inhibiting, preventing, reducing the severity of, delaying the onset of, reducing symptoms associated with the infection, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In some embodiments, the materials and methods of this disclosure produce protective immune responses to viral infection. In some embodiments, the term "protective immune response" against influenza virus refers to an immune response exhibited by an individual (e.g., a human) that is protective against disease when the individual is subsequently exposed to and/or infected with such, or alternative influenza virus. In some instances, the influenza virus (e.g., naturally circulating) can still cause infection, but it cannot cause a serious infection. Typically, the protective immune response results in detectable levels of host engendered serum and secretory antibodies that are capable of neutralizing virus of the same strain and/or subgroup (and possibly also of a different, non-vaccine strain and/or subgroup) in vitro and in vivo.

In some embodiments, the term "administering" refers to bringing a subject in contact with a compound of the present disclosure. As used herein, administration can be accomplished in vitro, i.e. in a test tube, or in vivo, i.e. in cells or tissues of living organisms, for example humans. In one embodiment, the present disclosure encompasses administering the compounds of the present disclosure to a subject.

In some embodiments the term "contacting" means that the indicated agent is introduced into a sample comprising immune cells in a test tube, flask, tissue culture, chip, array, plate, microplate, capillary, or the like, and incubated at a temperature and time sufficient to permit uptake of the agent.

In another embodiment, the term "contacting" refers to introducing the indicated agent into a subject, and the agent is allowed to come in contact with immune cells in vivo.

In some embodiments, the methods of this disclosure further comprise repeat contact of the cell with the polynucleotide or polypeptide, cell, vector, composition, liposome, etc. of this disclosure, which in some embodiments is prior to, during, or a combination thereof, infection of the subject with an influenza virus.

In some embodiments, the influenza virus is an H5N1 strain, which in some embodiments is a product of virus reassortant.

In some embodiments, the polynucleotide or polypeptide, cell, vector, composition, liposome, etc. of this disclosure is for use in treating any influenza infection, for example, infection with a virus similar to that deposited in NCBI's Genbank, accession numbers AF036358-AF036360, AF036362, AF036363, AF084261-AF084270, AF084276-AF084278, AF084282 AF084287, AF115284-AF115289 and AF115290-AF115295.

In some embodiments, the subject is protected against subsequent infection with an influenza virus of an alternate clade or subclade than that causing infection in said subject.

The compositions may be administered in any effective, convenient manner including, for instance, administration by intravenous, intraperitoneal, intramuscular, subcutaneous, intranasal or intradermal routes among others. In therapy or as a prophylactic, the active agent may be administered to an individual as an injectable composition, for example as a sterile aqueous dispersion, preferably isotonic. The compositions may be administered by injection, in some embodiments, to achieve a systematic effect against relevant viral pathogens. In some embodiments, the polypeptides, polynucleotides, vectors, cells, liposomes can be administered prophylactically or therapeutically, in an immunologically effective amount and in an appropriate carrier or excipient to stimulate an immune response specific for one or more strains of influenza virus sequence. In some embodiments, the carrier or excipient is a pharmaceutically acceptable carrier or excipient, such as sterile water, aqueous saline solution, aqueous buffered saline solutions, aqueous dextrose solutions, aqueous glycerol solutions, ethanol, or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

In some embodiments, the polynucleotide or polypeptide, cell, vector, composition, liposome, etc. of this disclosure stimulate an immune response by ex vivo or in vivo targeting of antigen presenting cells, such as, for example, dendritic cells. For example, proliferating dendritic cells are exposed to the polynucleotide or polypeptide, cell, vector, composition, liposome, etc. of this disclosure, in a sufficient amount and for a sufficient period of time to permit capture of the influenza antigens by the dendritic cells. The cells are then transferred into a subject to be vaccinated by standard intravenous transplantation methods.

In some embodiments, the polynucleotide or polypeptide, cell, vector, composition, liposome, etc. of this disclosure stimulate a protective immune response with a single dose is preferred, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type influenza infection. Similarly, adults who are particularly susceptible to repeated or serious influenza infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

In some embodiments, the polynucleotide or polypeptide, cell, vector, composition, liposome, etc. of this disclosure comprise, or are administered with one or more adjuvants for enhancing the immune response to the influenza antigens. Suitable adjuvants include: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvant QS-21.

In some embodiments, the polynucleotide or polypeptide, cell, vector, composition, liposome, etc. of this disclosure comprise, or are administered with one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered concurrent with the polynucleotide or polypeptide, cell, vector, composition, liposome, etc. of this disclosure or can be administered separately.

In some embodiments, the polynucleotide or polypeptide, cell, vector, composition, liposome, etc. of this disclosure are used for therapeutically and/or prophylactically treating a disease or disorder, typically influenza, by targeting immune cells in vitro, ex vivo or in vivo.

In some embodiments, the polynucleotide or polypeptide, cell, vector, composition, liposome, etc. of this disclosure serve as vaccines. In some embodiments, the term "vaccine," refers to a composition which elicits an immune response (cellular and/or humoral) in a subject. A vaccine may reduce the risk of infection but does not necessarily prevent infection. In specific, non-limiting embodiments, a vaccine increases the level of cellular and/or humoral immunity by at least 30 percent, 50 percent, or 100 percent of baseline levels.

In some embodiments, the vaccine may include live virus, where the virus has been weakened, or attenuated, such that it cannot cause disease; killed-virus; one or more additional viral proteins; chimeric viruses and other viral elements. This disclosure provides, in some embodiments, for the vaccination of an individual with the polynucleotide or polypeptide, cell, vector, composition, liposome, etc. of this disclosure, which in turn, induces cross-protection against influenza virus of different strains and/or subgroups. In some embodiments, the vaccines of this disclosure can optionally be combined with vaccines that induce protective immune responses against other infectious agents.

In some embodiments, vaccination is by any route known in the art, including but not limited to mucosal vaccination, such as intranasal or aerosol administration. For administration to mammals, and particularly humans, it is expected that the physician will determine the actual dosage and duration of treatment, which will be most suitable for an individual and can vary with the age, weight and response of the particular individual.

EXAMPLES

Materials and Methods

Consensus Sequence Design

A consensus HA nucleotide sequence (HAc) was deduced from the HA gene of approximately 500 H5N1 virus strains and a phylogenetic analysis was conducted (FIG. 1). Codon usage was optimizied for the consensus HA nucleotidesequence. The optimized nucleic acids were synthesized and constructed for expression with appropriate vectors, one of which was pVAX (Invitrogen, Carlsbad, Calif.). Using the consensus sequence as a template, plasmids encoding individual HA genes in each WHO vaccine were constructed. As a result, all nucleotide sequences encoding HAs, including the consensus HA (pHAc) and the HAs of different influenza virus strains, were codon-optimized and used in parallel in these studies.

Construction of Clade-Specific Sequence Design

A HA sequence was constructed for H5 of RG2 (H5N1 clade 2, subclade 1), and the nucleotide sequence (ID5) subsequently can be optimized for mammalian expression. Upon challenge with lethal dose of RG2, 100% of pID5 immunized mice were protected and only 40% of HAc immunized mice survived (FIGS. 15A-15F).

A HA sequence was also constructed for H5 of RG5 (reassortant of Anhui strain H5N1 (Anhui/01/2005(H5N1)/PR8-IBCDC-RG5). Indonesia/5/2005) strain (H5N1 clade 2, subclade 3). (Anhui). Starting from the existing DNA plasmid expressing HA of A/Duck/Fujian/1734 (FJ-like) as a template, the two strains differ in the following three amino acid residues: V281M; I231T, M293K. Site-directed mutagenesis was utilized to generate the desired DNA plasmid. After two injections, all mice immunized with 30 µg of pHAc or pAnhui developed significant anti-H5 antibodies against consensus HA and HA of RG5, respectively. Upon challenge with maximally available dose of RG5, 20% of control mice died while 100% of immunized with pHAc or pAnhui were protected Immunization with pAnhui protected the mice from significant loss of body temperature and body weight, which were evident in the control mice (FIGS. 15G-15L).

Characterization of Codon-Optimized HA Plasmids in Cultured Cells

The expression levels of the codon-optimized DNA vaccines were monitored in vitro. Human epithelial kidney 293 cells (HEK293 cells) were transfected with individual plasmids. After 48 hours, the cells were collected for SDS-PAGE analysis and the HA expression levels (including consensus HA coded for by HAc) were detected by immunoblotting with anti-HA antibodies (FIG. 8A).

The hemagglutination facilitated by the consensus HA coded for by HAc was also examined with hemadsorption assays. HEK293 cells were transfected with individual DNA vaccines coding for various HAs for 48 hours and then incubated with chicken red blood cells. The absorbed red blood cells were then lysed and the amount of hemoglobin was measured by optical density at 540 nm, to evaluate hemadsorption ability. (FIG. 8B).

Immunogenicity Determination

BALB/c mice were immunized with one or two injections of 30 ng DNA at a 3-week interval. The humoral immunogeneicity of the HA polypeptide expressed via translation of the HAc polynucleotide was monitored by serum antibody titer by ELISA assay, using soluble HA as the coating antigen. Soluble HA was obtained by expressing an HA ectodomain fused with a human Fc region in HEK293 cells and the medium thus generated was used for coating the ELISA plates. Cytotoxicity was also determined using splenocytes from immunized mice. Single cell suspensions were prepared by standard methodology, and ELISPOT assays were conducted by standard methodology. Splenocytes were cocultured with cells pulsed with or without peptide, incubated at 37° C. for 24 h on membrane filtration plates coated with anti-mouse γ interferon (IFN-γ). These plates were processed as previously described (McGettigan, J. P., et al. 2003. J. Virol. 77:237-244), and the spots were counted using an automated reader (FIGS. 9A-9C). In addition, the cell-based immune response facilitated by HAc immunization was assessed. (FIGS. 10 A-B).

FIG. 10(A) quantitates the cell-mediated immunity induced by the DNA vaccine by ELIspot assay. The splenocytes were obtained from a subject that was immunized with consensus HAc polynucleotide and in vitro stimulated with an HA-specific CD8-responsive peptide (HA 9mer) or an irrelevant peptide (HIV 9mer). FIG. 10 illustrates the increase in IFN-γ released by CD-8 positive T cells in response to an in vitro stimulation of HA peptide (HA 9mer), indicating the induction of the cell-mediated immunity by the HAc nucleotide vaccine.

FIG. 10(B) further illustrates cellular immunity responses subsequent to HAc immunization. In FIG. 10(B), viral challenge of mouse splenocytes with HA—expressing viruses post—immunization with HAc nucleotide vaccine resulted in a robust cell-mediated immune response, shown by an increase in IFN-γ released by CD8-positive T cells and assayed via ELIspot.

Virus Challenge Studies

Vaccinated mice were challenged with lethal doses of live NIBRG-14 (a Vietnam reassortant), RG2 (representing clade 2.1 H5N1), and RG5 (representing clade 2.3 H5N1) and survival was monitored. Mouse weight and febrility were also assessed. (FIGS. 11, 12, 15).

Neutralization Assays

HA-pseudotyped viruses were generated using an HIV backbone further comprising H5N1 HAs, including VN 1104, VN 1203, HK2003, Qing Hai, Indonesia and Tamsui, were used. Viral neutralization by antisera obtained from mice immunized twice with the construct was assessed. (FIGS. 13, 14).

Example 1

Construction of a Consensus Sequence

There are more than 700 hemagglutinin genes (HA) of H5N1 virus available in public databases. A remaining hurdle in H5N1 vaccine development is the lack of cross-protection between different viral strains. H5N1 viruses have been classified into different clades suggested by the WHO. To date, H5N1 vaccines are protective against viral infection with the same clade, and not viruses of another clade. For example, the Vietnam vaccine strain could induce full protection against itself, but fails to induce protective immunity against an Indonesia H5N1 strain. Therefore, in order to cover the genetic variability and thus induce cross-protection across different H5N1 strains, it was desirable to deduce a consensus sequence for protection studies, as well as to develop several additional isolated isolated nucleotide sequences that could be administered simultaneously so as to further broaden scope of protection against viral challenge.

A phylogenetic analysis of the consensus HA versus HA of WHO H5N1 vaccine strains was thus conducted (FIG. 1). Viral strains in red (08 Indonesia/5/2005 (NIBRG-2); 010 turkey/Turkey/1/2005 (NIBRG-23); 011 ws/Mongolia/244/2005; 012 bhg/Qinghai/1A/2005; 014 Anhui/1/2005) are WHO H5N1 vaccine strains, while those in blue (Consensus (HAc); 009 ck/Indonesia/5/2004 (ID); 013 bhg/Qinghai/62/205 (QH); 018 dk/China/E319-2/03 (Tamsui strain); 015 dk/Fujian/1734/05 (FJ-like)) designate vaccines that were constructed for characterization and challenge studies herein. Purple strains are both WHO H5N1 vaccine strains and strains pursued for vaccine design herein. (001 VN/1203/2004; 002 VN/1194/2004 (NIBRG-14); 003 HK/213/03 (HK). Stars indicate live H5N1 viruses tested in protection studies herein.

A consensus HA protein sequence was deduced from the HA gene of approximately 500 H5N1 virus strains (SEQ ID NO: 1) (FIG. 2). The consensus HA is located between Clade 1 and Clade 2 in the phylogenetic analysis, and is characterized by the amino acid sequence shown in SEQ ID: 1 and the nucleic acid sequence shown in SEQ ID:2 (FIGS. 2, 3).

Every species has a preferred codon usage that most genes use to encode proteins and this codon bias is related to gene expression efficiency in different species. For examples, influenza genes are rich in AT percentages whereas mammalian codons are GC-rich. Codon usage for the HA-based DNA vaccine encoding consensus HAs were thus optimized to maximize their expression in mammals (FIG. 3), using standard methodology. pVAX backbone vectors were utilized, and the HAc cassette was introduced thereto, the resulting construct was then termed "pHAc". Using the pHAc template, a series of plasmids encoding individual HA genes of WHO strains were constructed. As a result, all the HAs, including the consensus HA and the HA of different influenza virus strains, were codon-optimized and used in parallel in studies as described herein. FIGS. 4-5 depict an isolated polypeptide HA (SEQ ID NO:3) and an optimized, isolated polynucleotide (SEQ ID NO: 4)(ID5) coding for the isolated polypeptide of SEQ ID NO: 5, utilized in generating immunogenecity against H5N1 clade 2, subclade 1 viruses and subsequently utilized as a plasmid construct (pID5) as above. FIGS. 6-7 depict an isolated polypeptide HA (SEQ ID NO:5) and an optimized, isolated polynucleotide (SEQ ID NO: 6) (pAnhui) coding for the isolated polypeptide of SEQ ID NO: 3, utilized in generating immunogenecity against H5N1 clade 2, subclade 3 viruses and subsequently utilized as a plasmid construct (pAnhui) as above.

Example 2

Characterization of the Consensus Sequence

The expression levels of the codon-optimized DNA vaccines were monitored in HEK293 cells (FIG. 8A), as well as the ability of DNA vaccine-mediated HA receptor upregulation to facilitate hemagglutination (FIG. 8B). HEK293 cells expressing the consensus HA exhibited comparable hemadsorption ability to that of HAs of H5N1 viruses.

Example 3

Humoral and Cellular Immununogenicity of the Consensus Sequence

HAc polynucleotide vaccine was highly immunogenic, as determined by BALB/c mice immunization with HAc (in this example, via pHAc) in terms of serum antibody titer production. The endpoint antibody titer after one injection was between 1:400 and 1:1,600, whereas the titer was greater than 1:10,000 following two injections (FIGS. 9 A, B). Endpoint Ab titer also increased following a second vaccination (FIG. 9C).

ELISPOTs of CD8 cells indicated that HAc vaccination also indirectly induced copious amounts of IFN-γ, in response to subsequent priming with an HA peptide (FIGS. 10A, B).

Example 4

HAc Protects Against Lethal Challenge with H5N1

To assess the efficacy of the DNA vaccine, vaccinated mice were challenged with a lethal dose of live NIBRG-14, a Vietnam reassortant (H5N1 clade 1) virus, 14 days after the 2nd DNA vaccine injection and the survival was monitored. As shown in FIG. 11, one injection of the HAc polysaccharide vaccine (in this example, via pHAc) induced 70% protection against subsequent 100 $LD_{50}$ virus challenge while two injections conferred 100% protection. The mice were also afebrile following viral challenge, while the extent of body weight loss indicated the disease status of the mice correlated with survival observations (FIGS. 12A-12D).

Example 5

HAc Protects Against Lethal Challenge with Reassortant H5N1

In order to evaluate the cross-neutralization activity of antisera raised against HAc—coded consensus HA, HA pseudotyped virus of an HIV backbone was generated comprising various H5N1 HAs, and cross-neutralization activity of antisera raised against the HAc-encoded consensus HA polypeptide was assessed. The HA from six H5N1 strains, including VN 1104, VN1203, HK2003, Qing Hai, Indonesia and Tamsui, were used. Notably, the infectivity of all of these 6 pseudotyped viruses on MDCK cells were neutralized by antisera obtained from mice given two doses of immunization with the consensus HAc polynucleotide sequence. The half maximal effective concentration for 50% inhibition of pseudovirus infectivity ranged from dilution quotients of 1:175 to dilution quotients of 1:16,857 whereas the infectivity of VSV-G pseudotyped virus was not suppressed, showing the specificity of the antisera (FIGS. 13B-13M). Thus HAc DNA vaccination conferred protection against multiple H5N1 clades, which provides the advantage of cross protection by immunization with just HA—encoding polynucleotide, in comparison to use to date of whole virus vaccines with a restricted range of protective immunity. As seen in FIG. 14, HAc polynucleotide administration (in this example via pHAc) also confers immunity as shown by inhibition of chicken red blood cell hemadsorption in the presence of antisera raised against HAc-encoded HA polypeptide.

Example 6

Combinations of HAc, ID5 and Anhui Polynucleotide Sequences May Confer Broader Spectrum Protection Against H5N1 Resortment Viral Challenge In order to evaluate whether certain alternative isolated polynucleotide sequences provided improved protection against viral challenge from certain resortment H5N1 viral clades and subclades, BALB/c mice were immunized with 2 doses of pHAc, pID5, pAnhui, and pVAX (control). After subsequent challenge, mice vaccinated with pID5 showed increased protection against RG2 (clade 2, subclade 1) reassortant virus challenge, while mice immunized with pAnhui showed increased protection against RG5 (clade 2, subclade 3) reassortant virus challenge.

While certain features of the disclosure have been illustrated and described herein, many modifications, substitutions, changes, and equivalents will now occur to those of ordinary skill in the art. It is, therefore, to be understood that the appended claims are intended to cover all such modifications and changes as fall within the true spirit of the disclosure.

---

SEQUENCE LISTING

<160> NUMBER OF SEQ ID NOS: 6

<210> SEQ ID NO 1
<211> LENGTH: 568
<212> TYPE: PRT
<213> ORGANISM: Influenza A virus

<400> SEQUENCE: 1

```
Met Glu Lys Ile Val Leu Leu Phe Ala Ile Val Ser Leu Val Lys Ser
1               5                   10                  15

Asp Gln Ile Cys Ile Gly Ser His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270
```

```
Val Lys Lys Gly Asp Ser Thr Ile Met Lys Ser Glu Leu Glu Tyr Gly
            275                 280                 285
Asn Cys Asn Thr Lys Cys Gln Thr Pro Met Gly Ala Ile Asn Ser Ser
290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Arg Arg Lys Lys Arg Gly Leu Phe Gly Ala Ile
            340                 345                 350
Ala Gly Phe Ile Glu Gly Gly Trp Gln Gly Met Val Asp Gly Trp Tyr
            355                 360                 365
Gly Tyr His His Ser Asn Glu Gln Gly Ser Gly Tyr Ala Ala Asp Lys
370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
            435                 440                 445
Glu Asn Glu Arg Thr Leu Asp Phe His Asp Ser Asn Val Lys Asn Leu
450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Val Arg Asn Gly Thr Tyr Asp Tyr Pro Gln Tyr Ser Glu Glu Ala
            500                 505                 510
Arg Leu Lys Arg Glu Glu Ile Ser Gly Val Lys Leu Glu Ser Ile Gly
            515                 520                 525
Ile Tyr Gln Ile Leu Ser Ile Tyr Ser Thr Val Ala Ser Ser Leu Ala
530                 535                 540
Leu Ala Ile Met Val Ala Gly Leu Ser Leu Trp Met Cys Ser Asn Gly
545                 550                 555                 560
Ser Leu Gln Cys Arg Ile Cys Ile
                565

<210> SEQ ID NO 2
<211> LENGTH: 1704
<212> TYPE: DNA
<213> ORGANISM: Influenza A virus

<400> SEQUENCE: 2
atggagaaga tcgtgctgct gttcgccatc gtgagcctgg tgaagagcga ccagatctgc      60
atcggatccc acgccaacaa cagcaccgag caggtggaca ccatcatgga gaagaacgtg     120
accgtgaccc acgcccagga catcctggag aagacccaca acggcaagct gtgcgacctg     180
gacggcgtga agcctctgat cctgagagac tgcagcgtgg ccggctggct gctgggcaac     240
cctatgtgcg acgagttcat caacgtgcct gagtggagct acatcgtgga aaggccaac     300 cctgccaacg acctgtgcta ccctggcgac ttcaacgact acgaggagct gaagcacctg     360
ctgagcagaa tcaaccactt cgagaagatc cagatcatcc ctaagagcag ctggagcagc     420
cacgaggcca gcagcggcgt gagcagcgcc tgcccttacc agggcaagag cagcttcttc     480
```

```
agaaacgtgg tgtggctgat caagaagaac agcacctacc ctaccatcaa gagaagctac    540
aacaacacca accaggagga cctgctggtg ctgtggggca tccaccaccc taacgacgcc    600
gccgagcaga ccaagctgta ccagaaccct accacctaca tcagcgtggg caccagcacc    660
ctgaaccaga gactggtgcc taagatcgcc accagaagca aggtgaacgg ccagagcggc    720
agaatggagt tcttctggac catcctgaag cctaacgacg ccatcaactt cgagagcaac    780
ggcaacttca tcgcccctga gtacgcctac aagatcgtga agaagggcga cagcaccatc    840
atgaagagcg agctggagta cggcaactgc aacaccaagt gccagacccc tatgggcgcc    900
atcaacagca gcatgccttt ccacaacatc cccctctga ccatcggcga gtgccctaag    960
tacgtgaaga gcaacagact ggtgctggcc accggcctga aaacagccc tcagagagag   1020 agaagaagaa agaagagagg cctgttcggc gccatcgccg gcttcatcga gggcggctgg   1080
cagggcatgg tggacggctg gtacggctac caccacagca acgagcaggg cagcggctac   1140
gccgccgaca ggagagcac ccagaaggcc atcgacggcg tgaccaacaa ggtgaacagc   1200
atcatcgaca gatgaacac ccagttcgag gccgtgggca gagagttcaa caacctggag   1260
agaagaatcg agaacctgaa caagaagatg gaggacggct tcctggacgt gtggacctac   1320
aacgccgagc tgctggtgct gatggagaac gagagaaccc tggacttcca cgacagcaac   1380
gtgaagaacc tgtacgacaa ggtgagactg cagctgagag acaacgccaa ggagctgggc   1440
aacggctgct tcgagttcta ccacaagtgc gacaacgagt gcatggagag cgtgagaaac   1500
ggcacctacg actaccctca gtacagcgag gaggccagac tgaagagaga ggagatcagc   1560
ggcgtgaagc tggagagcat cggcatctac cagatcctga gcatctacag caccgtggcc   1620
agcagcctgg ccctggccat catggtggcc ggcctgagcc tgtggatgtg cagcaacggc   1680
agcctgcagt gcagaatctg catc                                          1704

<210> SEQ ID NO 3
<211> LENGTH: 568
<212> TYPE: PRT
<213> ORGANISM: Influenza A virus

<400> SEQUENCE: 3

Met Glu Lys Ile Val Leu Leu Ala Ile Val Ser Leu Val Lys Ser
1               5                   10                  15

Asp Gln Ile Cys Ile Gly Ser His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160
```

```
Arg Asn Val Val Trp Leu Ile Lys Lys Asn Asn Thr Tyr Pro Thr Ile
            165                 170                 175

Lys Lys Ser Tyr Asn Asn Thr Asn Gln Glu Asp Leu Leu Val Leu Trp
        180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
        210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
        290                 295                 300

Met Pro Phe His Asn Ile His Pro Leu Thr Ile Gly Glu Cys Pro Lys
305                 310                 315                 320

Tyr Val Lys Ser Asn Gln Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
        450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
        530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565
```

```
<210> SEQ ID NO 4
<211> LENGTH: 1701
<212> TYPE: DNA
<213> ORGANISM: Influenza A virus

<400> SEQUENCE: 4
atggagaaga tcgtgctgct gctcgccatc gtgagcctgg tgaagagcga ccagatctgc      60
atcggatccc acgccaacaa cagcaccgag caggtggaca ccatcatgga gaagaacgtg     120
accgtgaccc acgcccagga catcctggag aagacccaca cggcaagct gtgcgacctg      180 gacggcgtga agcctctgat cctgagagac tgcagcgtgg ccggctggct gctgggcaac     240
cctatgtgcg acgagttcat caacgtgcct gagtggagct acatcgtgga aaggccaac     300 cctaccaacg acctgtgcta ccctggctcc ttcaacgact acgaggagct gaagcacctg     360
ctgagcagaa tcaaccactt cgagaagatc cagatcatcc ctaagagcag ctggagcgac     420
cacgaggcca gcagcggcgt gagcagcgcc tgcccttacc tgggctcgcc agcttcttc      480 agaaacgtgg tgtggctgat caagaagaac agcacctacc ctaccatcaa gaaaagctac     540
aacaacacca ccaggagga cctgctggtg ctgtggggca tccaccacct caacgacgcc      600
gccgagcaga ccaagctgta ccagaaccct accacctaca tcagcatcgg caccagcacc     660
ctgaaccaga gactggtgcc taagatcgcc accagaagca aggtgaacgg ccagagcggc     720
agaatggact tcttctggac catcctgaag cctaacgacg ccatcaactt cgagagcaac     780
ggcaacttca tcgcccctga gtacgcctac aagatcgtga agaaggcga cagcgccatc     840 atgaagagcg agctggagta cggcaactgc aacaccaagt gccagacccc tatcggcgcc     900
atcaacagca gcatgccttt ccacaacatc caccctctga ccatcggcga gtgccctaag     960
tacgtgaaga gcaacagact ggtgctggcc accggcctga aaacagccc tcagagagag    1020 tcaagaagaa agagaggcct gttcggcgcc atcgccggct tcatcgaggg cggctggcag    1080
ggcatggtgg acggctggta cggctaccac cacagcaacg agcagggcag cggctacgcc    1140
gccgacaagg agagcaccca aaggccatc gacggcgtga ccaacaaggt gaacagcatc    1200
atcgacaaga tgaacaccca gttcgaggcc gtgggcagag agttcaacaa cctggagaga    1260
agaatcgaga acctgaacaa gaagatggag gacggcttcc tggacgtgtg gacctacaac    1320
gccgagctgc tggtgctgat ggagaacgag agaaccctgg acttccacga cagcaacgtg    1380
aagaacctgt acgacaaggt gagactgcag ctgagagaca cgccaagga gctgggcaac    1440 ggctgcttcg agttctacca caagtgcgac aacgagtgca tggagagcat cagaaacggc    1500
acctacaact accctcagta cagcgaggag gccagactga agagagagga gatcagcggc    1560
gtgaagctgg agagcatcgg cacctaccag atcctgagca tctacagcac cgtggccagc    1620
agcctggccc tggccatcat gatggccggc ctgagcctgt ggatgtgcag caacggcagc    1680
ctgcagtgca gaatctgcat c                                               1701

<210> SEQ ID NO 5
<211> LENGTH: 568
<212> TYPE: PRT
<213> ORGANISM: Influenza A virus

<400> SEQUENCE: 5

Met Gl

```
Asp Thr Ile Met Glu Lys Asn Val Thr Val Thr His Ala Gln Asp Ile
         35                  40                  45

Leu Glu Lys Thr His Asn Gly Lys Leu Cys Asp Leu Asp Gly Val Lys
 50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Ala Asn Asp Leu Cys Tyr Pro Gly Asn Phe Asn
                100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Asp His Glu Ala Ser
        130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Val Glu Tyr Gly
        275                 280                 285

Asn Cys Asn Thr Met Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460
```

-continued

```
Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 6
<211> LENGTH: 1701
<212> TYPE: DNA
<213> ORGANISM: Influenza A virus

<400> SEQUENCE: 6
atggagaaga tcgtgctgct gctcgccatc gtgagcctgg tgaagagcga ccagatctgc      60
atcggatccc acgccaacaa cagcaccgag caggtggaca ccatcatgga gaagaacgtg     120
accgtgaccc acgcccagga catcctggag aagacccaca acggcaagct gtgcgacctg     180
gacggcgtga agcctctgat cctgagagac tgcagcgtgg ccggctggct gctgggcaac     240
cctatgtgcg acgagttcat caacgtgcct gagtggagct acatcgtgga gaaggccaac     300
cctgccaacg acctgtgcta ccctggcaac ttcaacgact acgaggagct gaagcacctg     360
ctgagcagaa tcaaccactt cgagaagatc cagatcatcc ctaagagcag ctggagcgac     420
cacgaggcca gcagcggcgt gagcagcgcc tgcccttacc agggcacgcc cagcttcttc     480
agaaacgtgg tgtggctgat caagaagaac aacacctacc ctaccatcaa gagaagctac     540
aacaacacca accaggagga cctgctgatc ctgtggggca tccaccactc taacgacgcc     600
gccgagcaga ccaagctgta ccagaaccct accacctaca tcagcgtggg caccagcacc     660
ctgaaccaga gactggtgcc taagatcgcc accagaagca aggtgaacgg ccagagcggc     720
agaatggact tcttctggac catcctgaag cctaacgacg ccatcaactt cgagagcaac     780
ggcaacttca tcgcccctga gtacgcctac aagatcgtga agaaaggcga cagcgccatc     840
atgaagagcg aggtggagta cggcaactgc aacaccatgt gccagacccc tatcggcgcc     900
atcaacagca gcatgccttt ccacaacatc caccctctga ccatcggcga gtgccctaag     960
tacgtgaaga gcaacaaact ggtgctggcc accggcctga gaaacagccc tctgagagag    1020
agaagaagaa agagaggcct gttcggcgcc atcgccggct tcatcgaggg cggctggcag    1080
ggcatggtgg acggctggta cggctaccac cacagcaacg agcagggcag cggctacgcc    1140
gccgacaagg agagcaccca gaaggccatc gacggcgtga ccaacaaggt gaacagcatc    1200
atcgacaaga tgaacaccca gttcgaggcc gtgggcagag agttcaacaa cctggagaga    1260
agaatcgaga acctgaacaa gaagatggag gacggcttcc tggacgtgtg gacctacaac    1320
gccgagctgc tggtgctgat ggagaacgag agaaccctgg acttccacga cagcaacgtg    1380
aagaacctgt acgacaaggt gagactgcag ctgagagaca acgccaagga gctgggcaac    1440
ggctgcttcg agttctacca caagtgcgac aacgagtgca tggagagcgt gagaaacggc    1500
acctacgact accctcagta cagcgaggag gccagactga agagagagga gatcagcggc    1560
```

-continued

| | |
|---|---|
| gtgaagctgg agagcatcgg cacctaccag atcctgagca tctacagcac cgtggccagc | 1620 |
| agcctggccc tggccatcat ggtggccggc ctgagcctgt ggatgtgcag caacggcagc | 1680 |
| ctgcagtgca gaatctgcat c | 1701 |

The invention claimed is:

1. A method comprising:
providing a sufficient amount of at least one isolated polynucleotide selected from the group consisting of SEQ ID NO: 2, SEQ ID NO: 4, and SEQ ID NO:6 to a subject to induce an immune response against influenza.

2. The method of claim 1, wherein the subject's immune response is sufficient to protect the subject against influenza virus challenge.

3. The method of claim 2, wherein the influenza challenge strain is at least one of $H_1N1$ and H5N1.

4. A method of forming a glycosylated protein, the method comprising:

providing at least one polynucleotide selected from the group consisting of SEQ ID NO: 2, SEQ ID NO: 4, and SEQ ID NO:6 to one or more functioning cells; and utilizing the metabolic mechanisms within the cells to form the glycosylated protein corresponding to the polynucleotide.

5. The method of claim 4, wherein the one or more functioning cells are within a subject.

* * * * *